US012779166B2

(12) United States Patent
Zhao

(10) Patent No.: US 12,779,166 B2
(45) Date of Patent: Nov. 3, 2026

(54) DEVICES AND METHODS FOR ENHANCING INTRANASAL AIR AND ODORANT DELIVERY PATTERNS

(71) Applicant: OHIO STATE INNOVATION FOUNDATION, Columbus, OH (US)

(72) Inventor: Kai Zhao, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 803 days.

(21) Appl. No.: 18/297,495

(22) Filed: Apr. 7, 2023

(65) Prior Publication Data

US 2024/0024615 A1 Jan. 25, 2024

Related U.S. Application Data

(60) Provisional application No. 63/328,466, filed on Apr. 7, 2022.

(51) Int. Cl.
*A61M 21/00* (2006.01)

(52) U.S. Cl.
CPC ..... *A61M 21/00* (2013.01); *A61M 2021/0016* (2013.01); *A61M 2209/088* (2013.01); *A61M 2210/0618* (2013.01)

(58) Field of Classification Search
CPC .......... A61M 21/00; A61M 2021/0016; A61M 2209/088; A61M 2210/0618; A61F 5/08
USPC ...................................................... 600/26–28
See application file for complete search history.

(56) References Cited

U.S. PATENT DOCUMENTS

| | | | |
|---|---|---|---|
| 2,569,743 A | 10/1951 | Pomeroy | |
| 2,674,245 A | 4/1954 | Tanditter | |
| 3,935,859 A | 2/1976 | Doyle | |
| 5,105,807 A | 4/1992 | Kahn et al. | |
| 5,291,897 A | 3/1994 | Gastrin et al. | |
| 5,425,359 A | 6/1995 | Nan-Tien | |
| 5,601,594 A | 2/1997 | Best | |
| 6,390,089 B1 * | 5/2002 | Lacouture | A61F 5/08 606/204.45 |
| 6,478,026 B1 | 11/2002 | Wood | |
| 6,494,204 B1 * | 12/2002 | Ponce | A61M 15/085 128/203.18 |
| 6,561,188 B1 | 5/2003 | Ellis | |
| 6,561,193 B1 | 5/2003 | Noble | |
| 6,848,446 B2 | 2/2005 | Noble | |
| 7,506,649 B2 | 3/2009 | Doshi et al. | |

(Continued)

FOREIGN PATENT DOCUMENTS

| | | |
|---|---|---|
| CN | 102949769 | 3/2013 |
| WO | 2014/104066 | 7/2014 |

(Continued)

OTHER PUBLICATIONS

Li, Chengyu, et al. "Nasal structural and aerodynamic features that may benefit normal olfactory sensitivity." Chemical senses 43.4 (2018): 229-237.

(Continued)

*Primary Examiner* — Sunita Reddy
(74) *Attorney, Agent, or Firm* — Meunier Carlin & Curfman LLC

(57) ABSTRACT

Disclosed herein are devices, including nasal plugs and nasal clips, for modulating olfaction, as well as methods of using thereof to increase or decrease olfactory sensitivity.

6 Claims, 22 Drawing Sheets

(56) References Cited

U.S. PATENT DOCUMENTS

| | | | | |
|---|---|---|---|---|
| 7,727,186 | B2 | 6/2010 | Makower et al. | |
| 7,856,979 | B2 | 12/2010 | Doshi et al. | |
| 8,517,022 | B2 | 8/2013 | Halling et al. | |
| 10,010,442 | B2* | 7/2018 | Ierulli | A61F 5/08 |
| 10,029,058 | B2 | 7/2018 | Foote et al. | |
| 2004/0059368 | A1 | 3/2004 | Maryanka | |
| 2006/0207598 | A1* | 9/2006 | Thomas | A61F 5/08 128/207.18 |
| 2009/0048626 | A1* | 2/2009 | Beaudry | A61F 13/0253 602/54 |
| 2009/0194100 | A1 | 8/2009 | Minagi | |
| 2009/0205640 | A1* | 8/2009 | Kehiaian | A61F 5/08 128/200.24 |
| 2009/0308398 | A1 | 12/2009 | Ferdinand | |
| 2010/0030252 | A1* | 2/2010 | Stewart | A61F 5/08 606/199 |
| 2011/0034950 | A1* | 2/2011 | Toriumi | A61M 15/085 606/199 |
| 2011/0270297 | A1* | 11/2011 | Judd | A61M 29/00 606/199 |
| 2012/0046607 | A1 | 2/2012 | Syk | |
| 2012/0204870 | A1 | 8/2012 | McAuley et al. | |
| 2012/0330345 | A1* | 12/2012 | Tasca | A61F 5/08 606/199 |
| 2015/0173933 | A1* | 6/2015 | Castillo | A61F 5/08 606/204.45 |
| 2016/0128863 | A1 | 5/2016 | Loomas et al. | |
| 2017/0119990 | A1 | 5/2017 | Vygon | |
| 2017/0172783 | A1* | 6/2017 | Pepper | A61F 5/08 |
| 2018/0064892 | A1* | 3/2018 | Nelson | A61M 15/08 |
| 2018/0236201 | A1 | 8/2018 | Nussbaum et al. | |
| 2019/0167464 | A1* | 6/2019 | Lovato | A61F 5/08 |
| 2020/0069321 | A1 | 3/2020 | Zhao | |
| 2023/0072399 | A1 | 3/2023 | Zhao et al. | |

FOREIGN PATENT DOCUMENTS

| | | |
|---|---|---|
| WO | 2018/165372 | 9/2018 |
| WO | 2021/168285 | 8/2021 |

OTHER PUBLICATIONS

Uldry, et al., Sniff nasal inspiratory pressure in patients with chronic obstructive pulmonary disease. Eur Respir J 1997; 10: 1292-1296.
Heritier, et al., Sniff nasal inspiratory pressure. A noninvasive assessment of inspiratory muscle strength. Am J Respir Crit Care Med vol. 150. 1994, pp. 1678-1683.
Zhao, Kai, et al. "Perceiving nasal patency through mucosal cooling rather than air temperature or nasal resistance." PLoS One 6.10 (2011): e24618.
International Search Report and Written Opinion issued in PCT Application No. PCT/US2018/021464, dated Jun. 28, 2018.
International Preliminary Report on Patentability issued for Application No. PCT/US2018/021464, dated Sep. 19, 2019.
International Preliminary Report on Patentability issued in Application No. PCT/US2021/018824, dated Sep. 1, 2022.
International Search Report and Written Opinion, issued in Application No. PCT/US2021/018824 on May 19, 2021. 10 pages.
Office Action for U.S. Appl. No. 17/801,154 dated Sep. 5, 2024.
European Patent Office. Extended European search report. Issued in EP Application No. 21757729.5 on May 8, 2024. 10 pages.
European Patent Office. Communication pursuant to Rule 164(1) EPC. Issued in European Application No. 21757729.5 on Feb. 16, 2024. 12 pages.

* cited by examiner

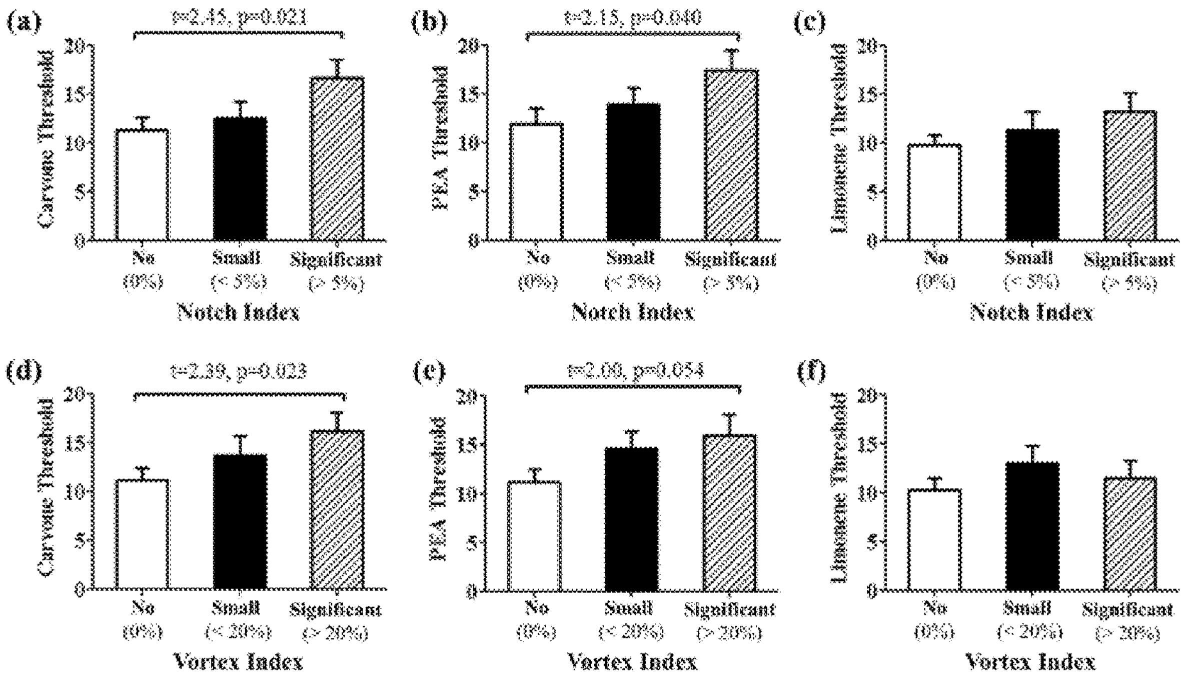
Figure 12
| | MCA | Nasal index | Notch index | Vortex index | ODT PEA | ODT D-Limonene | ODT L-Carvone |
|---|---|---|---|---|---|---|---|
| Nasal resistance | | | | | | | |
| MCA | | 0.56** | −0.54** | −0.47** | | | |
| Nasal index | | | −0.56** | −0.59** | | | |
| Notch index | | | | 0.76** | 0.32* | | 0.33* |
| Vortex index | | | | | | | 0.31* |
| ODT PEA | | | | | | 0.41** | 0.46** |
| ODT D-Limonene | | | | | | | 0.31* |
| ODT L-Carvone | | | | | | | |
*P < 0.05. **P < 0.01.
Figure 13
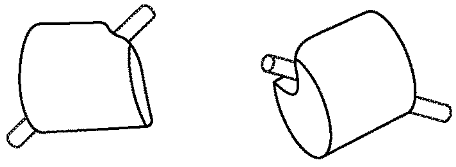
Figure 14A

DEVICES AND METHODS FOR ENHANCING INTRANASAL AIR AND ODORANT DELIVERY PATTERNS

CROSS-REFERENCE TO RELATED APPLICATIONS

This application claims benefit of U.S. Provisional Application No. 63/328,466, filed Apr. 7, 2022, which is hereby incorporated herein by reference in its entirety.

STATEMENT REGARDING FEDERALLY SPONSORED RESEARCH OR DEVELOPMENT

This invention was made with government support under R01 DC013626 awarded by the National Institutes of Health. The government has certain rights in the invention.

BACKGROUND

Smell, or olfaction, is a chemoreception that forms the sense of smell. Olfaction occurs when odorants bind to specific sites on olfactory receptors located in the nasal cavity. Glomeruli aggregate signals from these receptors and transmit them to the olfactory bulb, where the sensory input will start to interact with parts of the brain responsible for smell identification, memory, and emotion, ultimately resulting in the perception of odors. Olfaction has many purposes, such as the detection of hazards, pheromones, and the detection of desirable food. It integrates with other senses to form the sense of flavor. Thus, diminishment or loss of this sense can negatively impact quality of life. In spite of this, relatively few mechanisms for improving or restoring olfaction have been developed to date.

SUMMARY

Humans have developed many ways to enhance sensory function through peripheral mechanisms. For example, to enhance vision, humans have developed microscopes, telescopes, and eye glasses. These devices can enhance incoming light signals before they reach a viewer's eye(s), permitting the viewer to visually perceive objects that they otherwise might be unable to see. Likewise, megaphones, hearing aids, and the simple cupping of one's hand around one ear, can all serve to improve auditory perception. However, analogous devices and methods for enhancing the external odor signal have thusfar remained elusive.

Significant normative variations in both nasal anatomy and aerodynamics exist among healthy people—the most prominent being a narrowing of the upper nasal vestibule cartilage region (referred to as a "notch"). The magnitude of the notch also significantly correlates with measured odor detection thresholds among the subjects to many odors, meaning that individuals with a more significant "notch" would likely exhibit better olfaction (e.g., increase sensitivity towards odors). Further, a narrower vestibule region (e.g., at or about the "notch") can intensify the airflow vortex towards the olfactory region, resulting in greater olfactory sensitivity to high mucosal soluble odors.

Provided herein are devices that can induce changes in the anatomy and aerodynamics of the nasal cavity of a human subject so as to modulate olfaction.

For example, provided herein are devices, such as nasal plugs, which can direct and alter airflow through the nasal passages of a subject. In some embodiments, these devices can preferentially direct nasal airflow to the subject's olfactory epithelium, thereby enhancing olfactory sensitivity. In other embodiments, these devices can preferentially direct nasal airflow away subject's olfactory epithelium, thereby diminishing olfactory sensitivity. The devices can be used, for example, to alleviate symptoms of parosmia and/or phantosmia, including parosmia and/or phantosmia caused by an infection such as a SARS-CoV-2 infection.

Also provided herein are devices, such as nasal clips that, when applied to a subject's nose, pinch the subject's upper nasal vestibule cartilage, thereby constricting the subject's upper nasal vestibule to form or enhance a notch therewithin without completely blocking nasal airflow. Application of the device to the subject's nose can intensify the nasal airflow vortex with the subject's nasal vestibule airway, increase nasal airflow to the olfactory epithelium, or a combination thereof, thereby enhancing olfactory sensitivity.

In some embodiments, the nasal clip can comprise an outer clip frame comprising a first arm terminating in a first nose pad and a second arm terminating in a second nose pad. The first nose pad and the second nose pad can be spaced apart by a distance that allows the nasal clip to applied to the subject's nose so as to pinch the subject's upper nasal vestibule cartilage, thereby constricting the subject's upper nasal vestibule to form or enhance a notch therewithin without completely blocking nasal airflow.

In some embodiments, the nasal clip can further comprise an adjustable retention band bridging the first arm and the second arm within the outer clip frame. The adjustable retention band can be disposed (or positionable) within the outer clip frame at a distance spaced apart from the first nose pad and the second nose pad that affords seating and positioning of the nasal clip on the nose of the subject.

In some embodiments, the first nose pad and the second nose pad can be sized and spaced apart by a distance that allows the nasal clip to applied to the subject's nose so as to increase a notch index of the subject's nasal vestibule airway by at least 20%; increase a vortex index of the subject's nasal vestibule airway by at least 20%; apply a pinch to 15% to 60% of a height of the subject's nose; reduces the subject's nasal airflow by 15% to 80%; or any combination thereof.

Also provided are methods of using the devices described herein to modulate olfaction in a human subject.

For example, provided herein are methods of modifying olfaction in a human subject that comprise inserting a nasal plug into the subject's nasal nare. The nasal plug can comprise, for example, a pliable insert having a first surface and a second surface, a cross-section of the pliable insert sized to be accepted into and to fluidically seal the subject's nasal nare, the pliable insert having an axis therethrough from the first surface to the second surface; and a passage through the pliable insert from the first surface to the second surface, the passage having a distal end and a proximal end. In some embodiments, the proximal end of the passage is offset from the axis by an angle $\alpha$, where $\alpha>0°$ (e.g., where a is from 5° to 70° with respect to the first surface). Optionally, the nasal plug can further comprise a tube through the passage.

In some embodiments, the nasal plug can be disposed within the nasal nare in an "up" position, such that the tube preferentially directs nasal airflow to the subject's olfactory epithelium. In this arrangement, the nasal plug can enhance olfactory sensitivity.

In other embodiments, the nasal plug can be disposed within the nasal nare in a "down" position, such that the tube preferentially directs nasal airflow away from the subject's olfactory epithelium. In this arrangement, the nasal plug can decrease olfactory sensitivity (e.g., to alleviate symptoms of parosmia and/or phantosmia, including parosmia and/or phantosmia caused by an infection such as a SARS-CoV-2 infection).

Also provided herein are methods of enhancing olfaction in a human subject. These methods can comprise applying a nasal clip to the subject's nose to pinch the subject's upper nasal vestibule cartilage, thereby constricting the subject's upper nasal vestibule to form or enhance a notch therewithin without completely blocking nasal airflow. In some cases, application of the nasal clip can intensify a nasal airflow vortex with the subject's nasal vestibule airway, increase nasal airflow to the olfactory epithelium, or a combination thereof.

By way of example, as described herein, by applying a nasal clip to constrict the top anterior nasal vestibule of a subject's nose as shown in FIG. 1A, olfactory sensitivity can be dramatically enhanced. By way of example, as shown in FIG. 1B, application of a nasal clip described herein to a subject can significantly improve olfactory response, such as by increasing the subject's sensitivity to an odorant.

In some embodiments, the subject can have lower than average olfactory sensitivity prior to application of the nasal clip.

For example, in some embodiments, the subject's nasal vestibule airway can have a notch index of less than 5% before application of the nasal clip. In some embodiments, following application of the nasal clip, the subject's nasal vestibule airway can have a notch index of greater than 5%.

In some embodiments, application of the nasal clip can increase a notch index of the subject's nasal vestibule airway by at least 20%.

In some the subject's nasal vestibule airway has a vortex index of less than 20% before application of the nasal clip. In some embodiments, following application of the nasal clip, the subject's nasal vestibule airway can have a vortex index of greater than 20%.

In some embodiments, application of the nasal clip can increase the vortex index of the subject's nasal vestibule airway by at least 20%.

In some embodiments, the nasal clip applies a pinch to 15% to 60% of a protrusion height of the subject's nose.

In some embodiments, application of the nasal clip can reduce the subject's nasal airflow by 15% to 80%.

In some embodiments, the nasal clip can comprise an outer clip frame comprising a first arm terminating in a first nose pad and a second arm terminating in a second nose pad. The first nose pad and the second nose pad can be spaced apart by a distance that allows the nasal clip to applied to the subject's nose so as to pinch the subject's upper nasal vestibule cartilage, thereby constricting the subject's upper nasal vestibule to form or enhance a notch therewithin without completely blocking nasal airflow.

In some embodiments, the nasal clip can further comprise an adjustable retention band bridging the first arm and the second arm within the outer clip frame. The adjustable retention band can be disposed (or positionable) within the outer clip frame at a distance spaced apart from the first nose pad and the second nose pad that affords seating and positioning of the nasal clip on the nose of the subject.

DESCRIPTION OF DRAWINGS

As shown in FIG. 1B, subjects wearing a nasal clip possessed improved sensitivity to a sample odorant (phenylethyl alcohol, PEA, a common rose-like odor).

In FIG. 7B, point A indicates the deepest point of the nasal notch. The line BC is the extension line along the tangential direction of the anterior dorsal curve. The notch depth (h) is defined as the perpendicular distance from point A to line BC.

FIG. 12 includes plots showing the odor detection threshold (ODT) for L-Carvone (Panel A, Panel D), PEA (Panel B, Panel E), and D-Limonene (Panel C, Panel F). Subjects with significant nasal valve notch (notch index>5%) and more intense anterior airflow vortex (vortex index>20%) are likely to have better olfactory sensitivity to an odorant with high mucosal solubility (L-Carvone and PEA), but not an odorant with low mucosal solubility (D-Limonene).

FIG. 13 shows the Pearson correlation matrix between variables (n=44).

FIG. 14A shows an example of a nasal plug for use in improving olfaction.

DETAILED DESCRIPTION

Figure 1A:
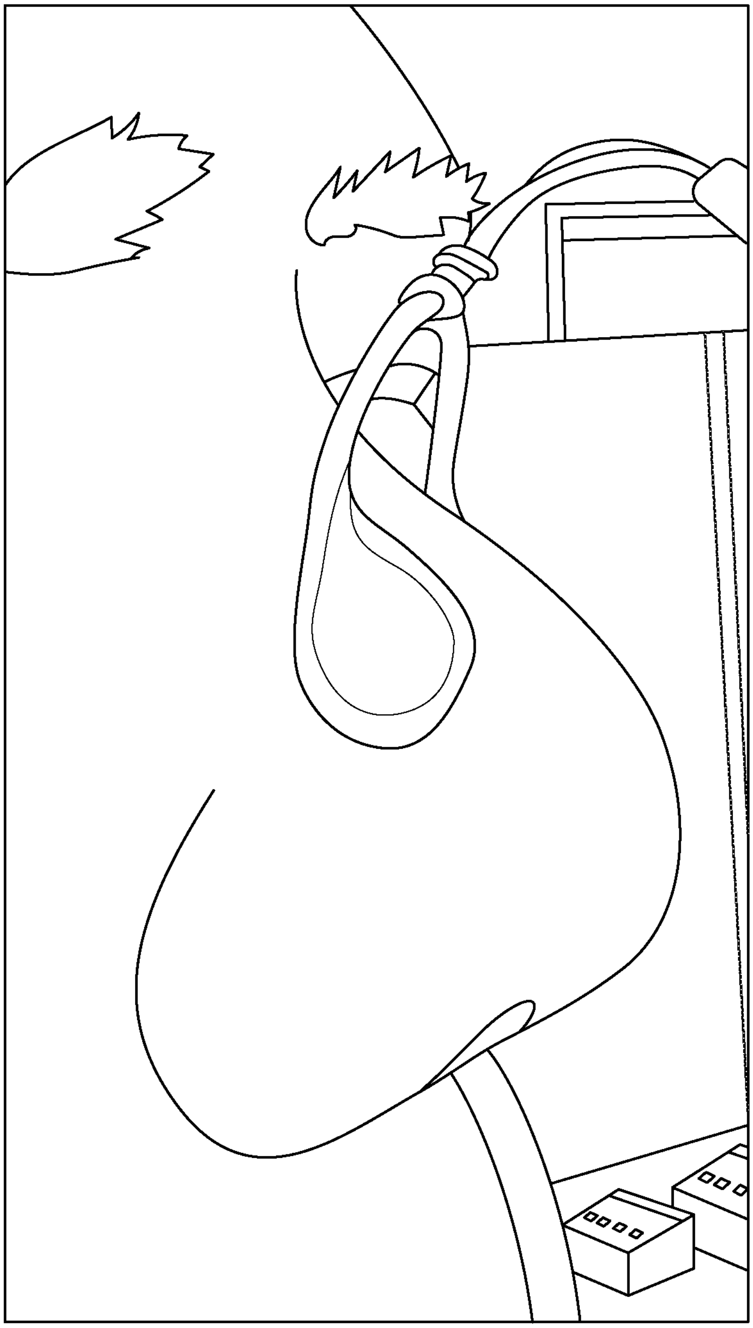
FIG. 1A illustrates an example nasal clip which can be applied to the exterior of a subject's nose to constrict the top anterior nasal vestibule of a subject's nose.
Figure 1B:
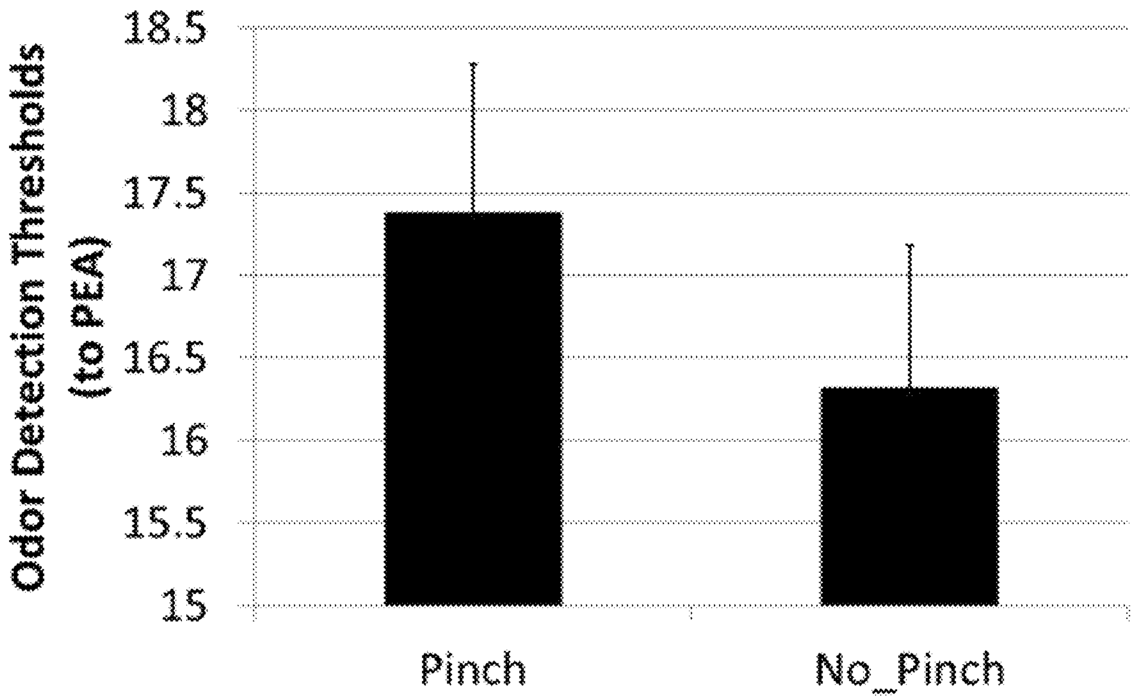
FIG. 1B is a plot detailing the improvement in olfactory response observed upon application of a nasal clip described herein to the nose of a subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Provided herein are methods of enhancing olfaction (e.g., improving olfactory sensitivity, for example, by increasing odor detection thresholds) in a human subject. These methods can comprise applying a nasal clip to the subject's nose to pinch the subject's upper nasal vestibule cartilage, thereby constricting the subject's upper nasal vestibule to form or enhance a notch therewithin without completely blocking nasal airflow.

Application of the nasal clip to the subject's nose can intensify the nasal airflow vortex with the subject's nasal vestibule airway, increases nasal airflow to the olfactory epithelium, or a combination thereof, thereby enhancing olfactory sensitivity.

In some embodiments, the subject can have lower than average olfactory sensitivity prior to application of the nasal clip.

The presence or magnitude of a notch within the upper nasal vestibule of a subject—both prior to applying a nasal clip and following application of a nasal clip—can be determined, for example, using the methods described in Example 1.

In some embodiments, the subject's nasal vestibule airway can have a notch index of less than 5% (e.g., less than 4.5%, less than 4%, less than 3.5%, less than 3%, less than 2.5%, less than 2%, less than 1.5%, less than 1%, or less than 0.5%) before application of the nasal clip. In some of these embodiments, following application of the nasal clip, the subject's nasal vestibule airway can have a notch index of greater than 5%.

In other embodiments, the subject's nasal vestibule airway can have a notch index of greater than 5% (e.g., greater than 5.5%, or greater than 6%) before application of the nasal clip.

In some embodiments, application of the nasal clip can increase the notch index of the subject's nasal vestibule airway by at least 5% (e.g., at least 10%, at least 15%, at least 20%, at least 25%, at least 30%, at least 40%, at least 50%, at least 75%, at least 100%, or more).

The presence or magnitude of a vortex index within the upper nasal vestibule of a subject—both prior to applying a nasal clip and following application of a nasal clip—can be determined, for example, using the methods described in Example 1.

In some the subject's nasal vestibule airway has a vortex index of less than 20% (e.g., less than 19%, less than 18%, less than 17%, less than 16%, less than 15%, less than 14%, less than 13%, less than 12%, less than 11%, less than 10%, less than 9%, less than 8%, less than 7%, less than 6%, or less than 5%) before application of the nasal clip. In some of these embodiments, following application of the nasal clip, the subject's nasal vestibule airway can have a vortex index of greater than 20% (e.g., greater than 21%, greater that 22%, greater than 23%, greater than 24%, or greater than 25%).

In other embodiments, the subject's nasal vestibule airway can have a vortex index of greater than 20% (e.g., greater than 22%, or greater than 25%) before application of the nasal clip.

In some embodiments, application of the nasal clip can increase the vortex index of the subject's nasal vestibule airway by at least 5% (e.g., at least 10%, at least 15%, at least 20%, at least 25%, at least 30%, at least 40%, at least 50%, at least 75%, at least 100%, or more).

In some embodiments, the nasal clip applies a pinch to from 15% to 60% of a protrusion height of the subject's nose (defined as the height along an axis extending frontally from the surface of the patients face towards the bridge of the patient's nose).

In some embodiments, application of the nasal clip can reduce the subject's nasal airflow by from 15% to 80%.

Examples of suitable nasal clips are described below.

Also provided herein are methods of modifying olfaction in a human subject that comprise inserting a nasal plug into the subject's nasal nare. The nasal plug can comprise, for example, a pliable insert having a first surface and a second surface, a cross-section of the pliable insert sized to be accepted into and to fluidically seal the subject's nasal nare, the pliable insert having an axis therethrough from the first surface to the second surface; and a passage through the pliable insert from the first surface to the second surface, the passage having a distal end and a proximal end. In some embodiments, the proximal end of the passage is offset from the axis by an angle $\alpha$, where $\alpha > 0°$ (e.g., where a is from 5° to 70° with respect to the first surface). Optionally, the nasal plug can further comprise a tube through the passage.

In some embodiments, the nasal plug can be disposed within the nasal nare in an "up" position, such that the tube preferentially directs nasal airflow to the subject's olfactory epithelium. In this arrangement, the nasal plug can enhance olfactory sensitivity.

In other embodiments, the nasal plug can be disposed within the nasal nare in a "down" position, such that the tube preferentially directs nasal airflow away from the subject's olfactory epithelium. In this arrangement, the nasal plug can decrease olfactory sensitivity (e.g., to alleviate symptoms of parosmia and/or phantosmia, including parosmia and/or phantosmia caused by an infection such as a SARS-CoV-2 infection).

Examples of suitable nasal plugs are described below.

Methods that enhance olfactory sensitivity can find application in a wide array of settings. For example, many individuals rely on their olfactory function for their occupation, including chefs, perfumers, food/wine critics, fragrance designers, sensory testing experts, etc. Acute and better olfactory function would greatly benefit their career development. Likewise, ordinary consumers may appreciate improved olfactory function at various times, such as to better enjoy food, wine, fragrances, etc.

Nasal Plugs

Example nasal plugs suitable for use in modifying olfaction are described, for example, in U.S. Patent Application Publication No. 2020/0069321, U.S. Patent Application Publication No. 2023/0072399, International Publication No. WO 2021/168285, and International Publication No. WO 2018/165372, each of which is hereby incorporated by reference herein in its entirety.

Figure 2A:
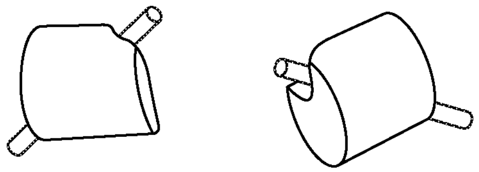
FIG. 2A shows an example of a nasal plug for use in modifying olfaction.
Figure 2B:
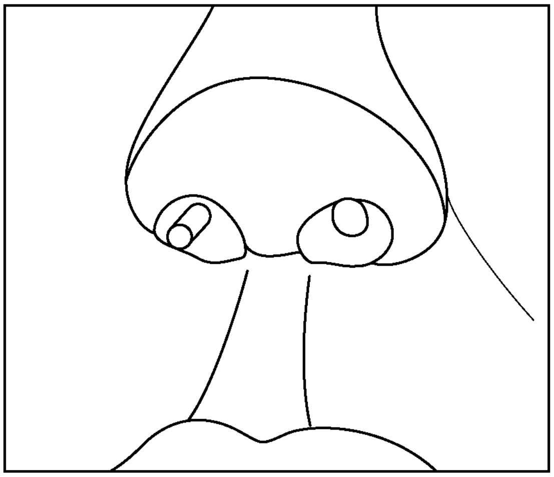
FIG. 2B shows the nasal plug of FIG. 14A as worn by a subject.
Figure 3A:
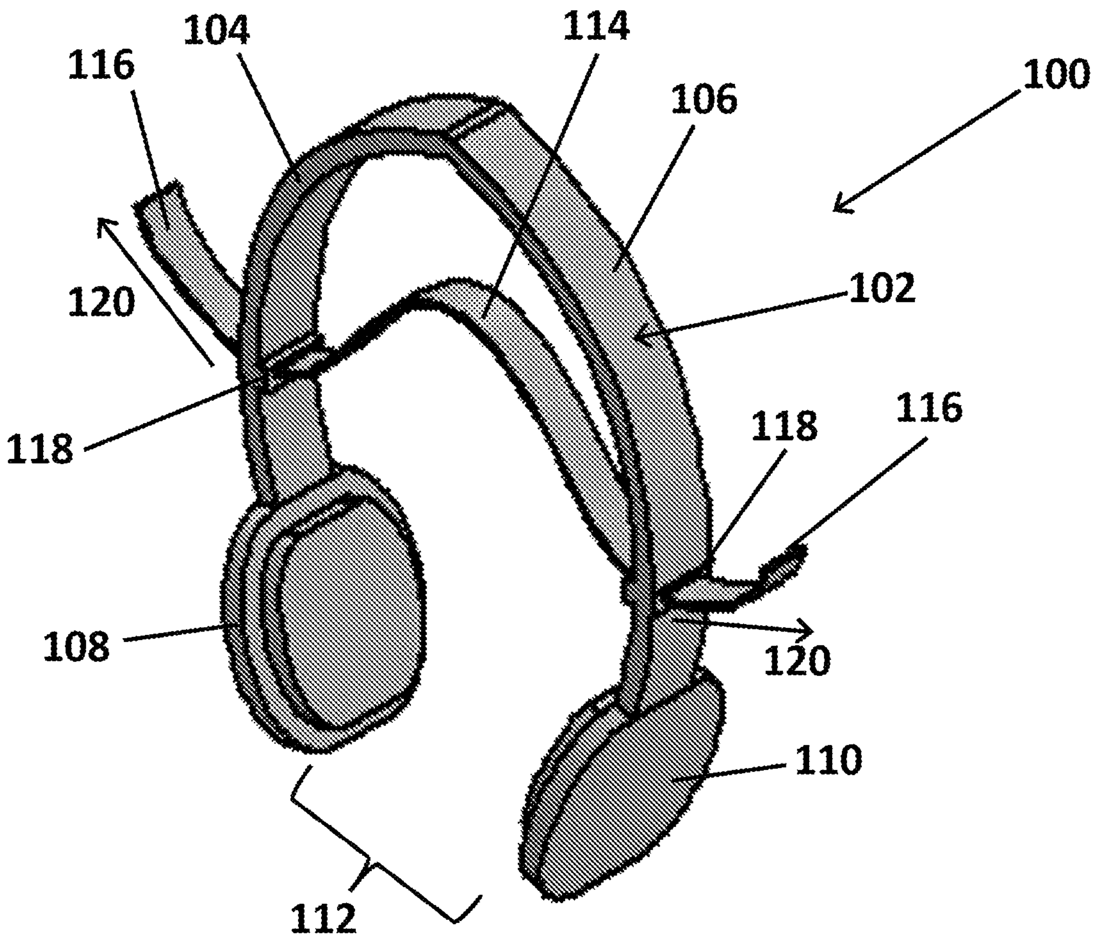
FIG. 3A illustrates a perspective view of an example nasal clip for enhancing olfaction.
Figure 3B:
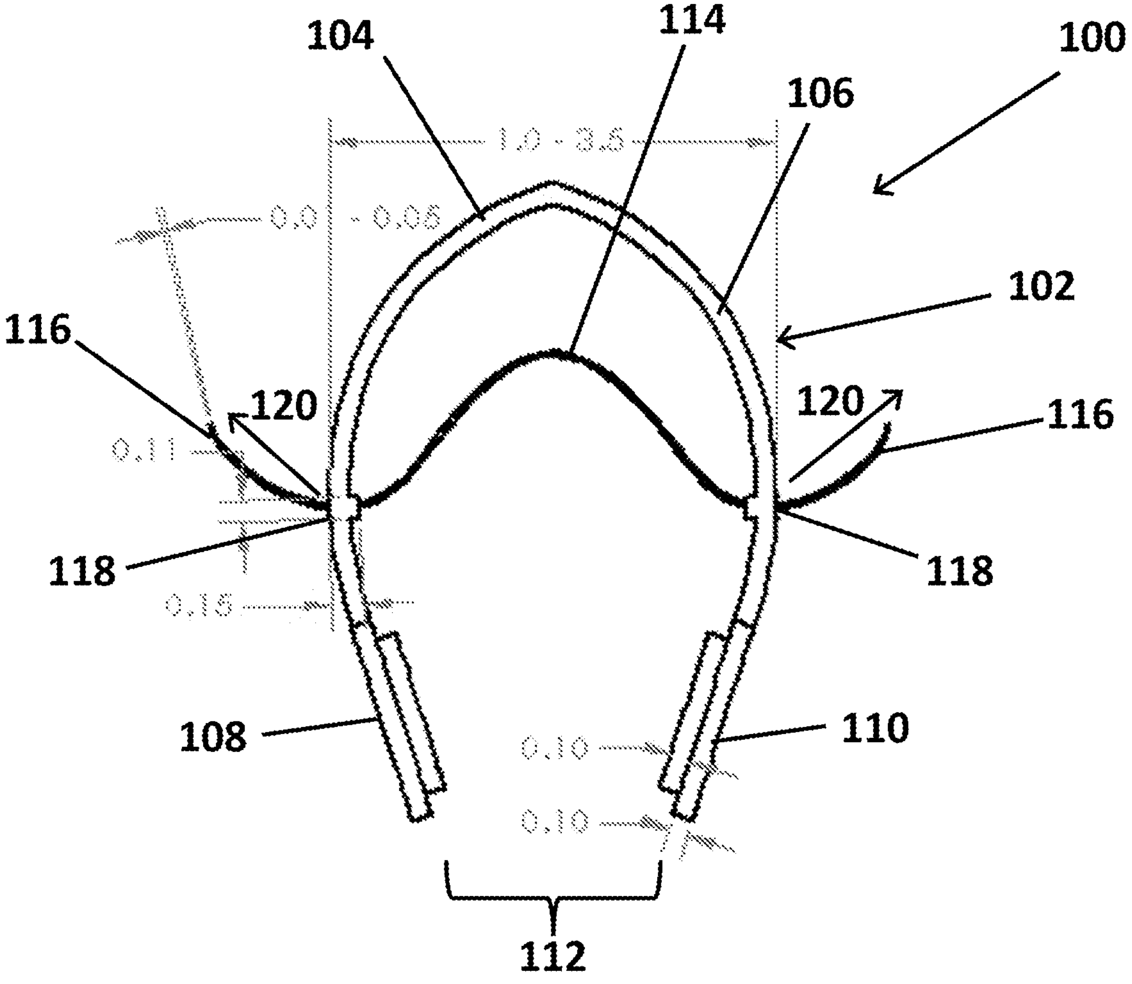
FIG. 3B illustrates a frontal view of an example nasal clip for enhancing olfaction.
Figure 3C:
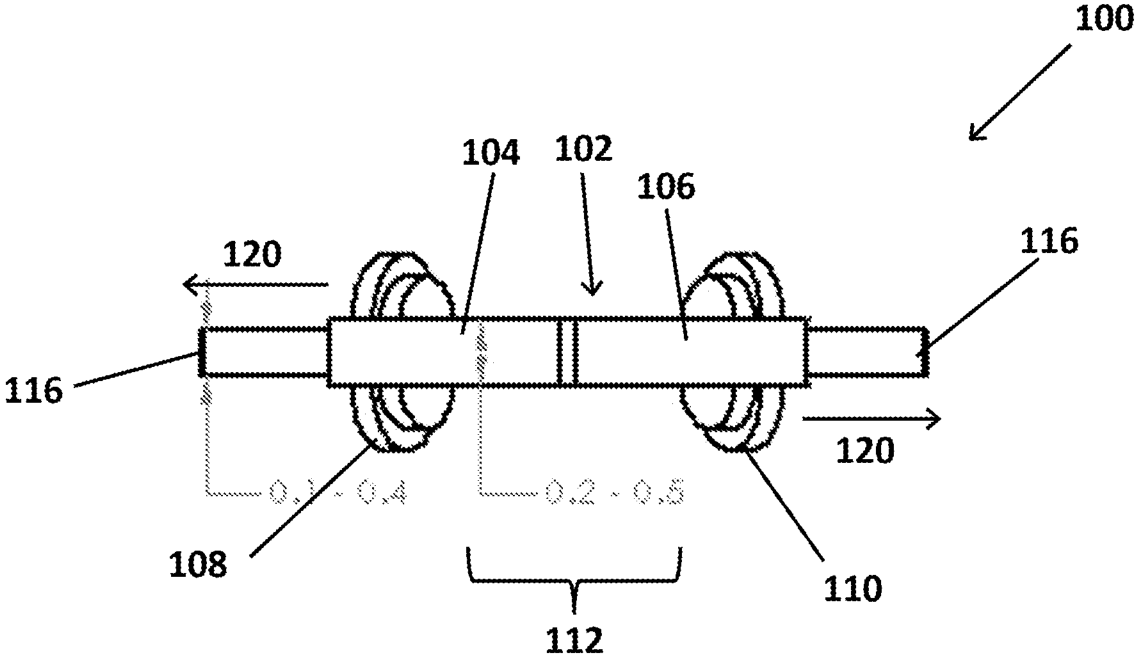
FIG. 3C illustrates a top view of an example nasal clip for enhancing olfaction.
Figure 3D:
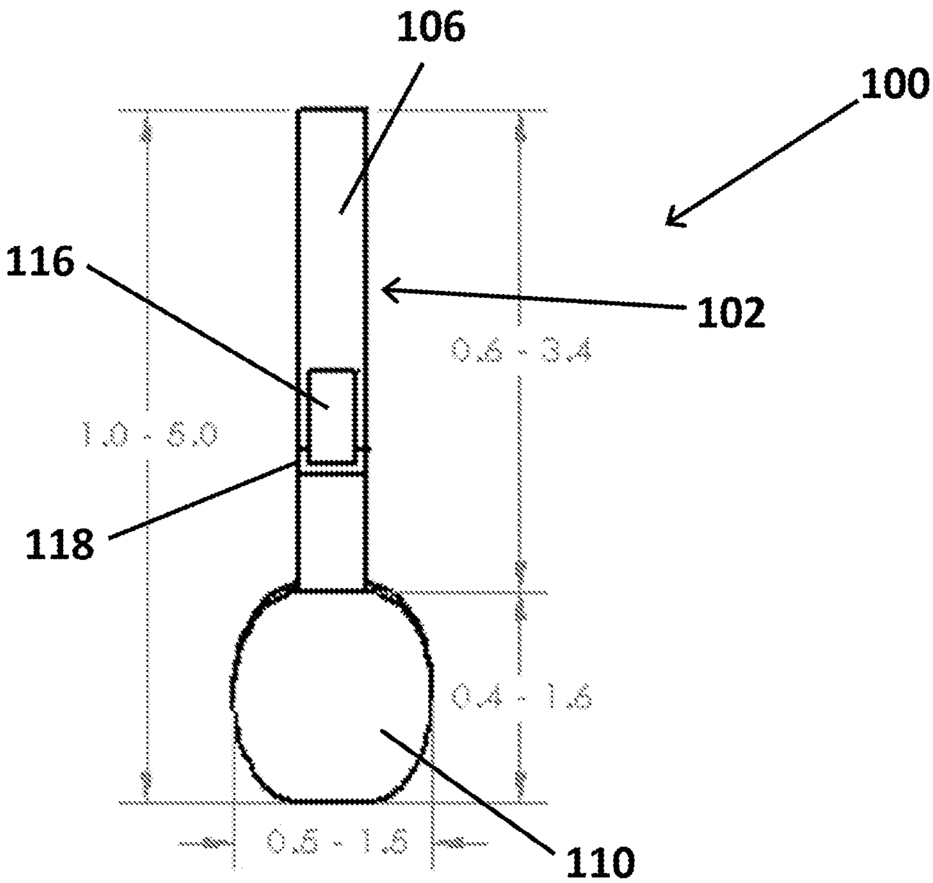
FIG. 3D illustrates a side view of an example nasal clip for enhancing olfaction.
Figure 4A:
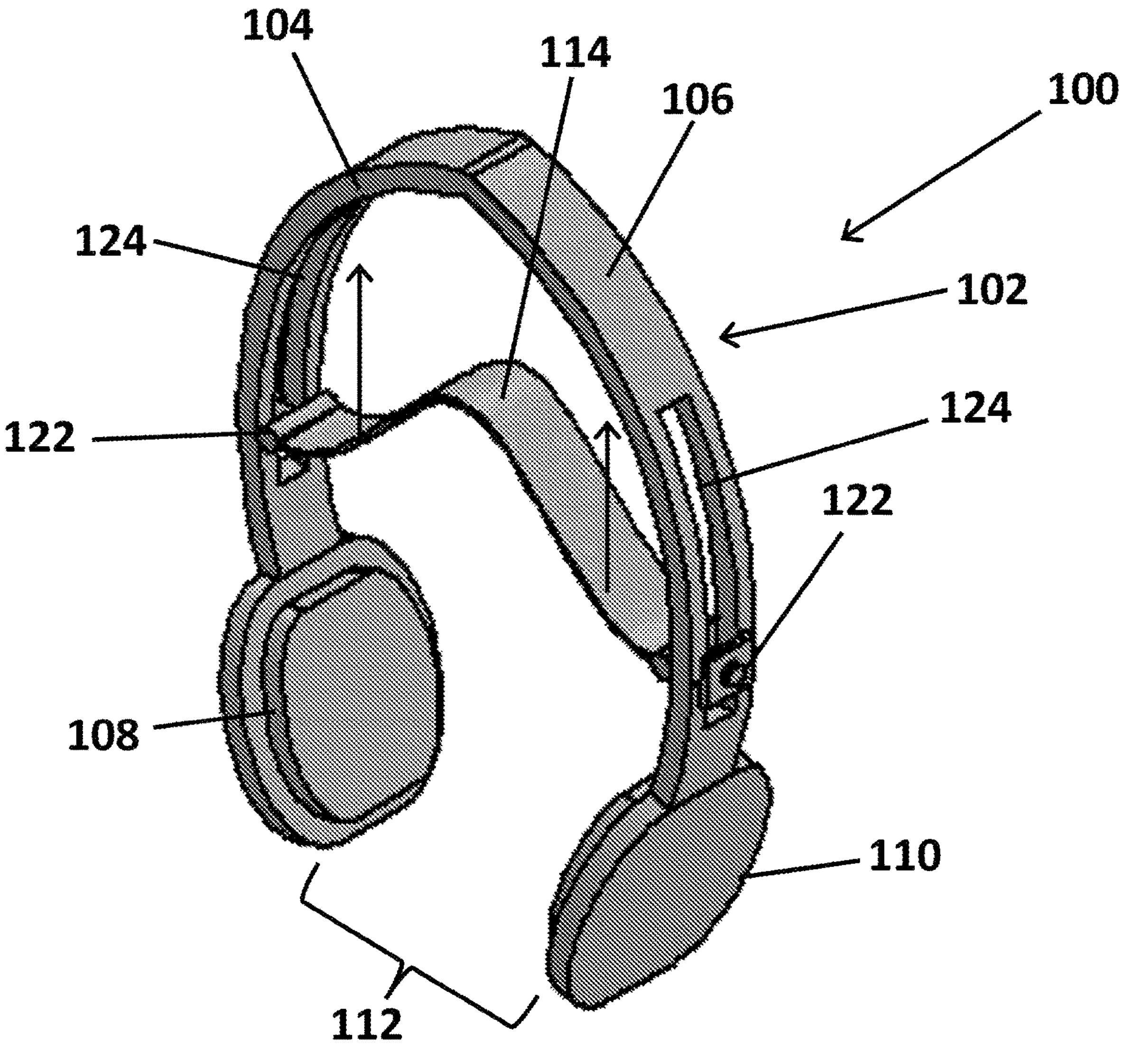
FIG. 4A illustrates a perspective view of an example nasal clip for enhancing olfaction.
Figure 4B:
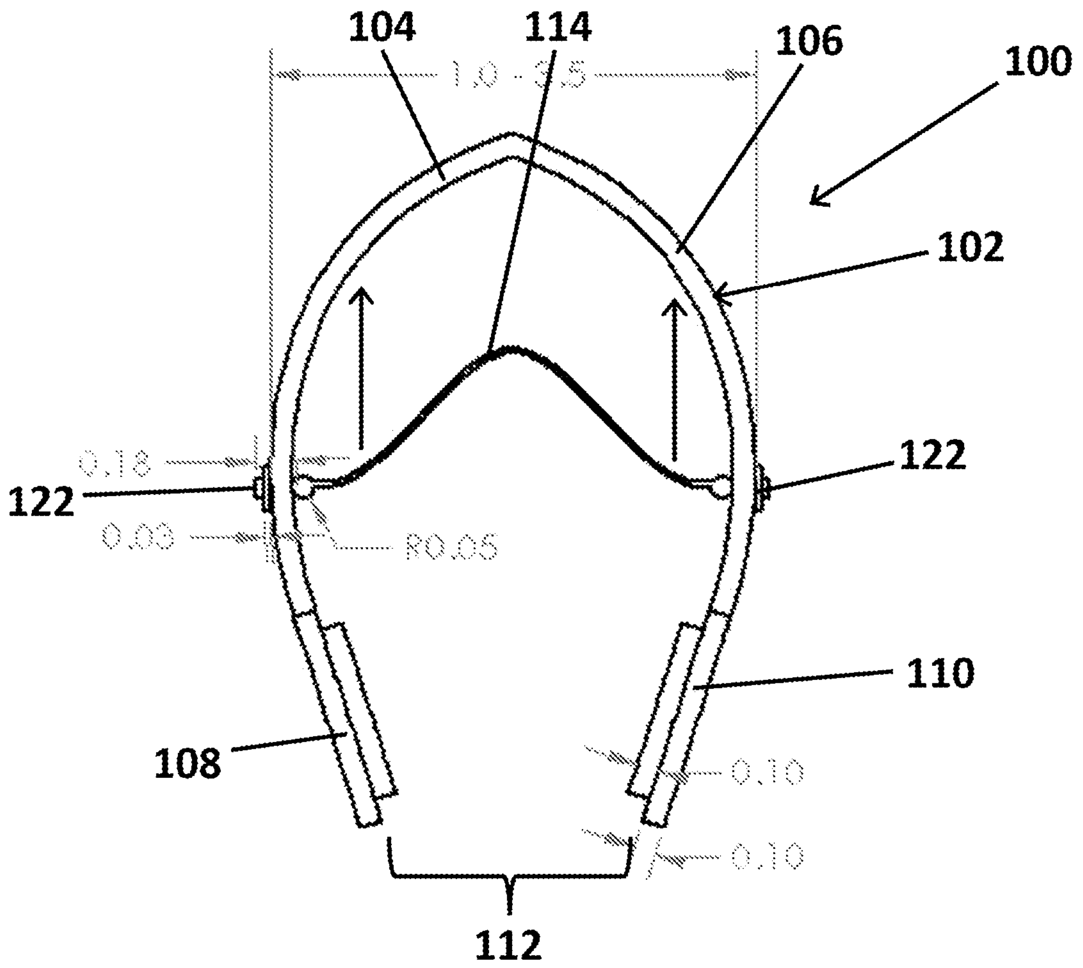
FIG. 4B illustrates a frontal view of an example nasal clip for enhancing olfaction.
Figure 4C:
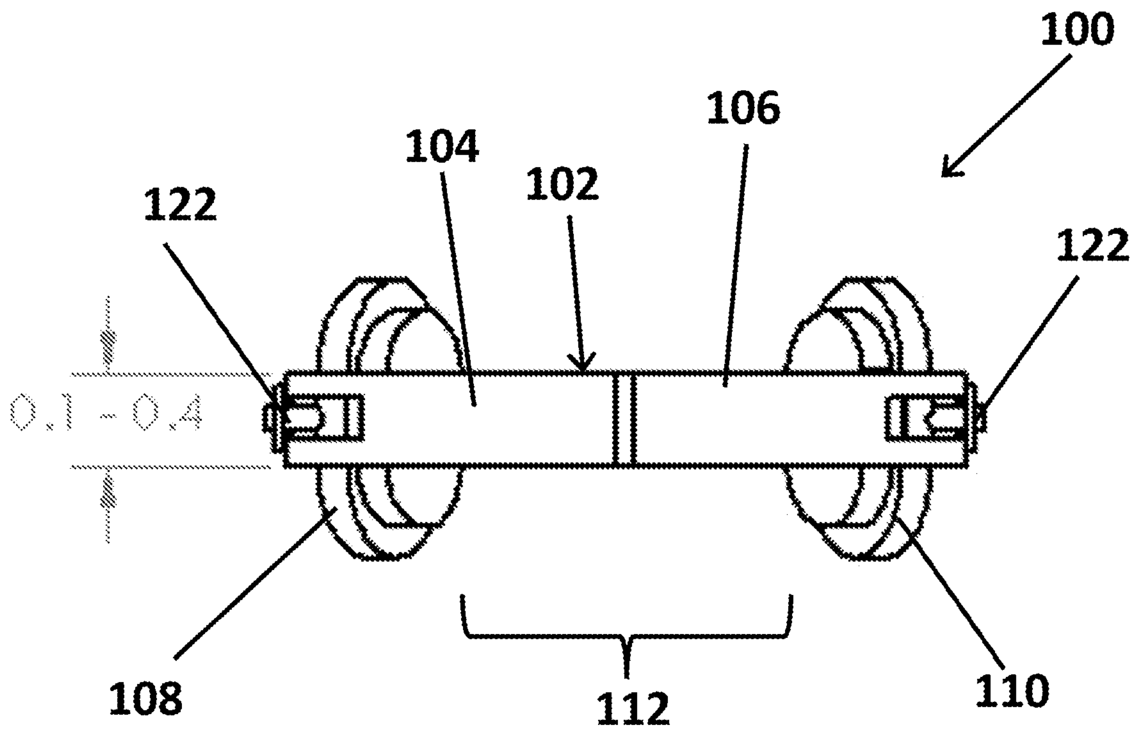
FIG. 4C illustrates a top view of an example nasal clip for enhancing olfaction.
Figure 4D:
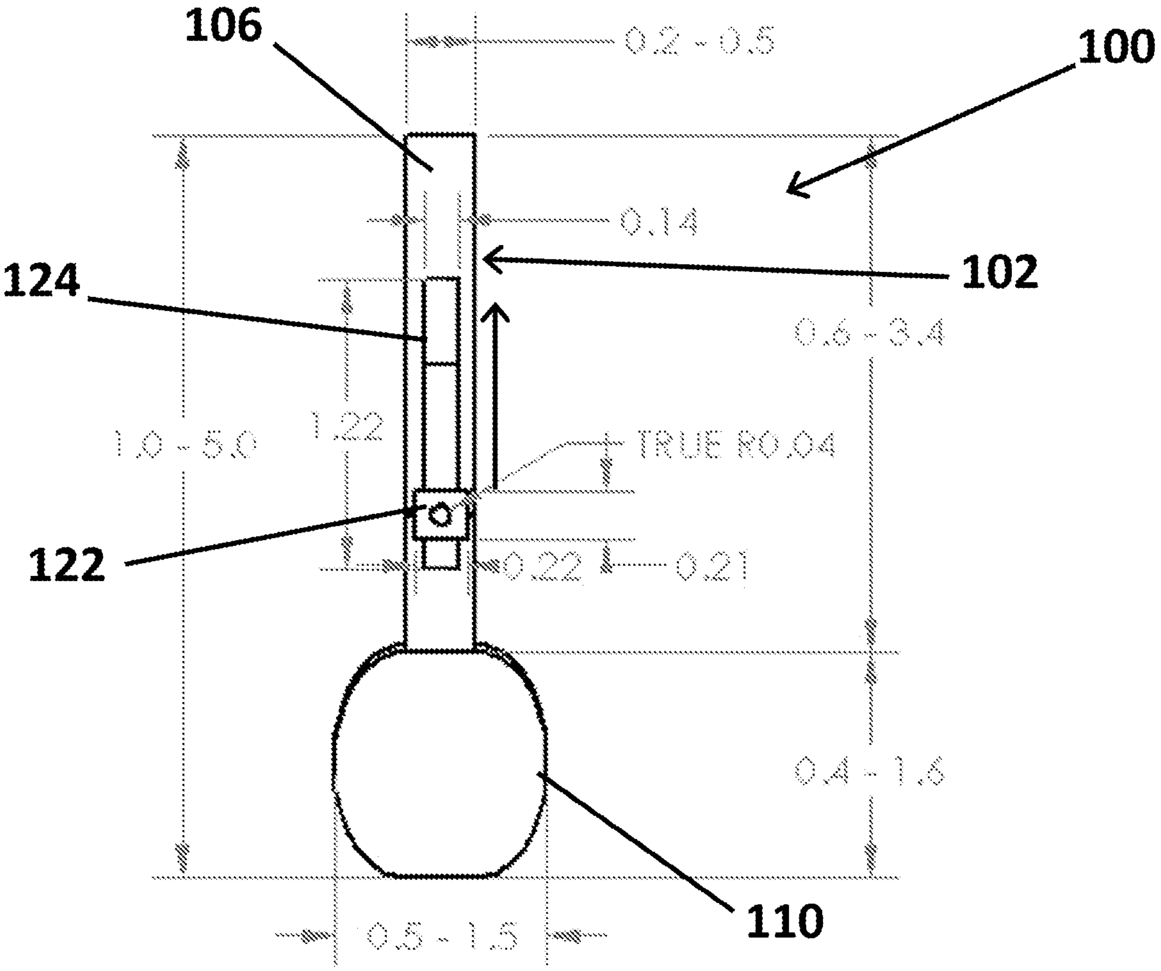
FIG. 4D illustrates a side view of an example nasal clip for enhancing olfaction.

Referring to FIGS. 2A-2B, the nasal plug can include a pliable "plug", as shown, a cylindrical profile, shaped to adapt to a nostril or nasal nare of a patient so as to substantially seal air flow. That is, the nasal plug itself, without further modification, would substantially cause the patient to be unable to breathe through a nostril into which it is inserted. As such, the actual profile of the nasal plug could be of any shape sufficient to block air flow, and such profile may dependent on the pliability of the nasal plug material. For example, if the nasal plug is made of a soft pliable foam, as illustrated in FIGS. 2A-2B, then the profile may be cylindrical, but could also be angular, e.g., rectangular, square, triangular or could be oval, spherical, or other shape suitable to block air passage through the nostril but for a passage for directing air flow. The nasal plug may be made of foam, silicon or any other soft material.

Referring to FIGS. 2A-2B, a passage is provided through the nasal plug from a distal end of the plug to a proximal end of the plug, where distal is used herein to be the portion of the plug that is external to a person once the plug is inserted into the person's nostril. The passage may include a tube or other support structure there through to provide additional stability and to maintain the passage or bore through the nasal plug. Such support structure can be integral or fixedly attached to the interior of the nasal plug passage or may be held in place by other methods, such as interference fit or friction fit, or may even be held in place by an adhesive. The tubes may be made of plastic or any material that can maintain the shape and structure. Although illustrated as cylindrical, the tube may be of any shape that provides appropriate airflow through the passage, such as conical or squares.

Figure 18:
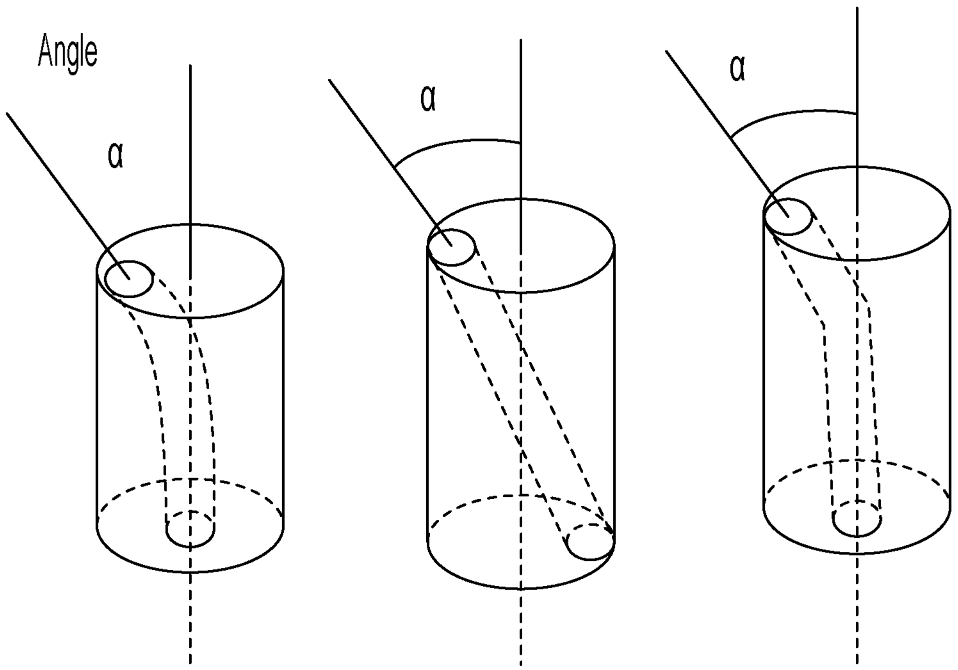
FIG. 18 shows various embodiments of the tube or passage of an example of a nasal plug with an exit portion at a predetermined angle relative to the axial direction of the plug.

The tube passing through the nasal plug, or the passage without the tube, has a predetermined angle with respect to an axial direction of the nasal plug to provide airflow to the nostril at a predetermined location within the sinuses. In the alternative of the entire tube or passage being at an angle through the entire length of the nasal plug, a portion of the tube or passage may be angled to provide an exit at the proximate end of the nasal plug at the appropriate predetermined angle $\alpha$. Various embodiments of the tube or passage with an exit portion at a predetermined angle to the axial direction of the plug is illustrated in FIG. 18. The predetermined angle $\alpha$ may be $>0°$ from a central axis (axial direction) of the nasal plug. The angle may range from about 5° to 70°.

Although not shown in the figures, a nasal foam plug may alternatively be a single piece for use in both nostrils of a patient. That is, the foam plug may be a single unit with two passages therethrough, each passage positioned to enter one of the subject's nostrils. This unitary nasal plug may include tubes or other a support structure through each passage to provide additional stability and to maintain the passage or bore through the nasal plug. Such support structure can be integral or fixedly attached to the interior of the nasal plug passage or may be held in place by other methods, such as interference fit or friction fit, or may even be held in place by an adhesive. Although illustrated as cylindrical, the tube may be of any shape that provides appropriate airflow through the passage.

Figure 14B:
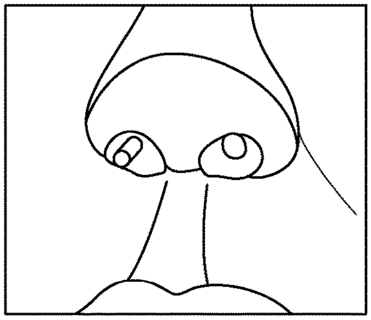
FIG. 14B shows the nasal plug of FIG. 14A as worn by a subject.
Figure 14C:
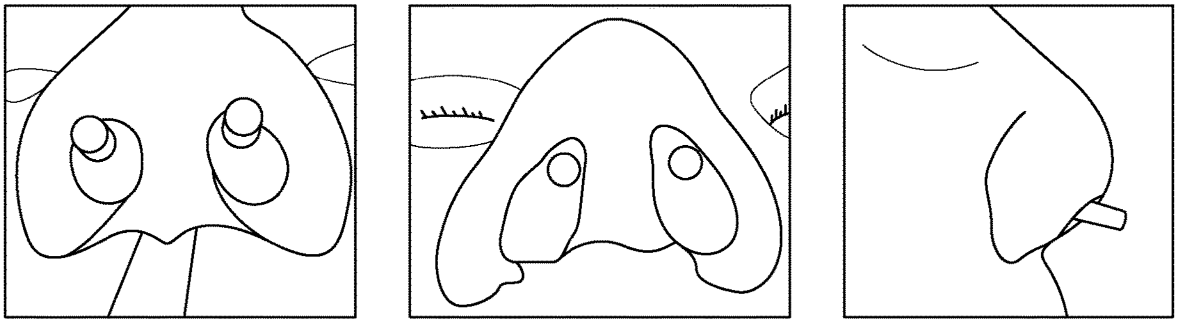
FIG. 14C shows (i) a view of the location of the tubes in a person's nares in a "down" position; (ii) an illustration of the positioning of the tube exit in a person's nares in the "down" position; and (iii) a side view of the patient with a nasal plug with the tube in the "down" position. "Down" refers to the airflow being directed to a lower portion of the nasal cavity of the patient.
Figure 14D:
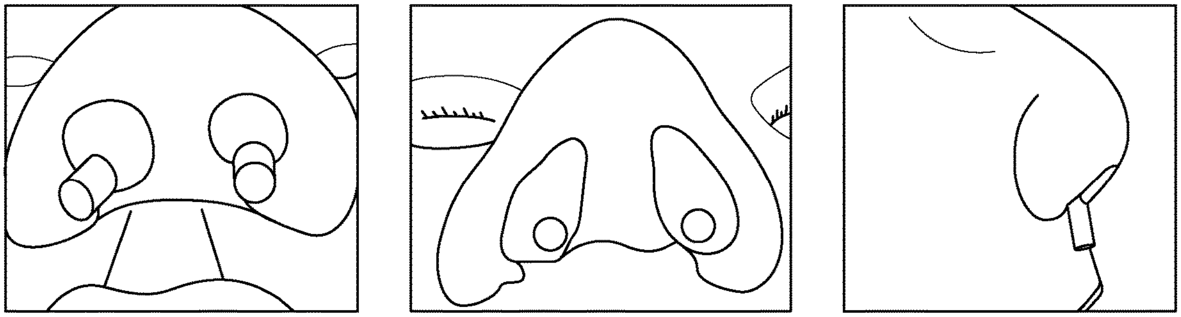
FIG. 14D shows (i) a view of the location of the tubes in a person's nares in a "up" position; (ii) an illustration of the positioning of the tube exit in a person's nares in the "up" position; and (iii) a side view of a person with a nasal plug with the tube in the "up" position. "Up" refers to the airflow being directed to an upper portion of the nasal cavity.

Referring to FIGS. 14C and 14D, the orientation nasal plugs within the nares may be adjusted by the user to direct airflow within the nasal passages. Turning or adjusting the plugs changes the angle at which the directed airflow enters the nasal passages of a subject.

FIG. 14C illustrates a "down" orientation of the airflow in which "down" refers to the airflow being directed to a lower portion of the nasal cavity of the patient. This orientation can preferentially direct nasal airflow away subject's olfactory epithelium, thereby diminishing olfactory sensitivity. Such devices can be used, for example, to alleviate symptoms of parosmia and/or phantosmia, including parosmia and/or phantosmia caused by an infection such as a SARS-CoV-2 infection.

FIG. 14D illustrates an "up" orientation of the air flow in which "up" refers to the airflow being directed to an upper portion of the nasal cavity of the patient. This orientation can preferentially direct nasal airflow to the subject's olfactory epithelium, thereby enhancing olfactory sensitivity.

While these two "orientations" are illustrated, the patient may find that and different orientation between "down" and "up" will provide the desired olfactory sensitivity.

In other embodiments, the nasal plug can comprise a nasal plug, such as a nasal plug described in U.S. Patent Application Publication No. 2023/0072399 or International Publication No. WO 2021/168285.

Nasal Clips

Suitable nasal clips include nasal clips that, when applied to a subject's nose, pinch the subject's upper nasal vestibule cartilage, thereby constricting the subject's upper nasal vestibule to form or enhance a notch therewithin without completely blocking nasal airflow. Application of such a device to the subject's nose can intensify the nasal airflow vortex within the subject's nasal vestibule airway, increase nasal airflow to the olfactory epithelium, or a combination thereof, thereby enhancing olfactory sensitivity. The nasal clips can be distinguished from traditional nasal clips for swimmers, for example, because they do not completely block the nasal airflow when worn.

Referring now to FIGS. 3A-3D and 4A-4D, in some embodiments, the nasal clip (100) can comprise an outer clip frame (102) comprising a first arm (104) terminating in a first nose pad (108) and a second arm (106) terminating in a second nose pad (110). The outer clip frame can have any suitable shape; however, in some embodiments, the outer clip frame can have a general u-shape. In some embodiments, the first arm and the second arm can be curved.

The first nose pad (108) and the second nose pad (110) can be spaced apart by a distance (112) that allows the nasal clip to applied to the subject's nose so as to pinch the subject's upper nasal vestibule cartilage, thereby constricting the subject's upper nasal vestibule to form or enhance a notch therewithin without completely blocking nasal airflow. In some embodiments, the distance can be adjustable.

The first elements of the outer clip frame, including the first arm and the second arm, can by fabricated from any suitable material (or combination of materials) that provides the desired degree of rigidity and flexibility so as to allow the nasal clip to be applied securely to the nose of a wearer and exert the requisite force on the subject's upper nasal vestibule cartilage to constrict the subject's upper nasal vestibule to form or enhance a notch therewithin without completely blocking nasal airflow.

In some embodiments, the nasal clip (100) can further comprise an adjustable retention band (114) bridging the first arm (104) and the second arm (106) within the outer clip frame (102). The adjustable retention band can be disposed (or positionable) within the outer clip frame at a distance spaced apart from the first nose pad and the second nose pad that affords seating and positioning of the nasal clip on the nose of the subject.

Referring to FIGS. 3A-3D, in some embodiments, the retention band (114) can be formed from a length of a soft or compliant material (e.g., elastomeric silicone) whose ends (116) extend through openings (118) within the outer clip frame (102). The relative portion of the retention band (114) present within the outer clip frame (102) can be adjusted by pulling or pushing (arrows, 120) the ends (116) to vary the length of the segment of the retention band present within the outer clip frame (and by extension the fit of the nasal clip). Referring to FIGS. 4A-4D, in other embodiments, the ends (122) of the retention band (114) can be coupled to a track (124) disposed on or within the outer clip frame, allowing the position of retention band to be adjusted relative to the first nose pad and the second nose pad.

In some embodiments, the first nose pad and the second nose pad can be sized and spaced apart by a distance that allows the nasal clip to applied to the subject's nose so as to increase a notch index of the subject's nasal vestibule airway by at least 20%; increase a vortex index of the subject's nasal vestibule airway by at least 20%; apply a pinch to 15% to 60% of a height of the subject's nose; reduces the subject's nasal airflow by 15% to 80%; or any combination thereof.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1: Characterization of Nasal Structural and Aerodynamic Features that Relate to Olfactory Sensitivity Nasal airflow that effectively transports ambient odors to the olfactory receptors is important for human olfaction. Yet, the impact of nasal anatomical variations on airflow pattern and olfactory function is not fully understood. In this Example, 22 healthy volunteers were recruited and underwent computed tomographic scans for computational simulations of nasal airflow patterns. Unilateral odor detection thresholds (ODT) to l-carvone, phenylethyl alcohol (PEA) and d-limonene were also obtained for all participants. Significant normative variations in both nasal anatomy and aerodynamics were found. The most prominent was the formation of an anterior dorsal airflow vortex in some but not all subjects, with the vortex size being significantly correlated with ODT of l-carvone ($r=0.31$, $P<0.05$). The formation of the vortex is likely the result of anterior nasal morphology, with the vortex size varying significantly with the nasal index (ratio of the width and height of external nose, $r=-0.59$, $P<0.001$) and nasal vestibule "notch" index ($r=0.76$, $P<0.001$). The "notch" is a narrowing of the upper nasal vestibule cartilage region. The degree of the notch also significantly correlates with ODT for PEA ($r=0.32$, $P<0.05$) and l-carvone ($r=0.33$, $P<0.05$). ODT of d-limonene, a low mucosal soluble odor, does not correlate with any of the anatomical or aerodynamic variables. This study revealed that nasal anatomy and aerodynamics can have a significant impact on normal olfactory sensitivity, with greater airflow vortex and a narrower vestibule region likely intensifying the airflow vortex toward the olfactory region and resulting in greater olfactory sensitivity to high mucosal soluble odors.

Background

Nasal airflow that effectively transports ambient airborne odorants to the olfactory receptors located in the superior region of the nasal cavity is a prerequisite for normal human olfactory function. It is well established that human olfactory acuity has significant variability, with much research focused on receptor genetics and postreceptor neural variations among subjects. However, the degree of variation in olfactory acuity that can be accounted for by differences in internal nasal anatomy and aerodynamics has seldom been addressed.

During a normal breath, less than 15% of the air inhaled flows through the olfactory region, and significant normative variations in both nasal anatomy and aerodynamics have been reported. The most prominent is the formation of an airflow vortex in the anterior dorsal region in some but not all subjects, with the intensity of the vortex recently reported to correlate significantly with the nasal index. Yet, direct associations between such aerodynamic variations and olfactory acuity have never been established, although studies of regional variation in nasal volume from computed tomographic (CT) scans have provided support for the notion that local volume changes in nasal airway may affect olfactory function. Studies using a three-dimensional anatomically accurate nasal cavity model based on one individual's CT scan also confirmed that, depending on the location, relatively minor changes in critical nasal regions may dramatically alter airflow distribution and greatly affect the ability of odorant molecules to access the olfactory epithelium. However, these were only theoretical calculations unsupported by human testing.

Historically, nasal anatomical variations have been reported as the nasal index, which is the ratio of the external nasal width and height. Ecogeographic variation in nasal index has been posed as an example of human morphological adaptation to climate, with broad noses (platyrrhine) evolving in habitats with warm, humid environments and narrow noses (leptorrhine) evolving in colder climates where the air needs more warming. These anterior nasal structure variations may also have an impact on airflow patterns, with narrower and taller external noses more likely to form intense anterior dorsal vortices. It has been reported distinct anatomical variations in the nasal vestibule (they termed it "notch") in another sample of healthy controls that may result in regional variations of aerodynamic resistance, although it is unclear whether the notch is related to the nasal index. The functional relevance of these anatomical and aerodynamic variations and their potential impact on olfactory function have not been investigated.

The understanding of normative peripheral mechanisms of olfactory function variability may have broad implications, for example, on the design human olfactory psychophysical tests and selection sensory panels in the flavor and fragrance industry, as well as in the clinical field, where nasal obstruction associated with nasal sinus disease is a prevalent cause of olfactory dysfunction. Yet, the association of nasal obstruction with olfactory loss cannot be fully understood without the knowledge of the impact of nasal anatomy and its variation among healthy subjects. Objective measures of nasal airflow (i.e., acoustic rhinometry or rhinomanometry) are capable of indexing only global airflow or static airway dimensions, and they correlate poorly with patients' subjective symptoms.

Computational fluid dynamic (CFD) modeling techniques have been used to quantify anatomical-dependent changes in nasal airflow pattern. In this Example, we characterize the functional impact of nasal aerodynamic variations on human olfaction with CFD approaches.

Materials and Methods

Human Subjects. 22 healthy subjects underwent CT scans for CFD modeling. The group consisted of 10 males and 12 females: 20 Caucasian, 1 African American, and 1 Asian American. Their ages ranged from 21 to 39 years, with a mean of 25.6, median of 24.5, and standard deviation (SD) of 4.84 years. Written informed consent was obtained from all volunteers. All of the participants underwent medical history screening to exclude pre-existing nasal sinus disease, severe seasonal or perennial allergies, prior olfactory complaint, head trauma, and prior nasal surgery. Both acoustic rhinometry and rhinomanometry were performed immediately before the CT scan on all subjects to objectively confirm the absence of severe nasal obstruction. Genetic diversity in functioning olfactory receptors has been reported between African Americans and non-African Americans, but in this small sample, subject enrollment was predominantly Caucasian.

Unilateral odor detection thresholds. Within the same visit, unilateral olfactory thresholds for three commonly encountered odorants (l-carvone [minty], phenylethyl alcohol [PEA, rose-like], and d-Limonene [orange-like]) were obtained for all participants. These odorants were selected due to their distinct sorptive properties in nasal mucus: d-limonene is quite insoluble, whereas PEA and l-carvone are highly soluble, although experimental data in mucus only exists for l-carvone. Animal studies have demonstrated that as airflow rate decreases, neural responses to more sorptive odors are more affected (diminished) than those to less sorptive odors. A similar effect in humans was reported, where the perceived intensity of an odorant classified as more sorptive (l-carvone) was lower when perceived through the nostril with the lower nasal-cycle flow rate relative to the higher flow rate nostril. On the basis of this evidence, we hypothesized that sensitivity to highly soluble odorants (PEA and l-carvone) would be more affected by variations in nasal anatomic and aerodynamic features than would sensitivity to the less soluble d-limonene.

Thresholds for all three odorants were determined through a two-alternative, forced-choice, stair-case method. Each odorant series consisted of 24 bottles of differing concentrations, beginning with a neat solution (step 0) and extending in half-log (for PEA) or binary (for 1-Carvone and d-Limonene) dilution steps in glycerol for 23 steps. The head space airborne odorant concentration for each dilution sample was calibrated and measured using gas chromatography. The threshold was measured in one nostril while the other was blocked by a foam plug, then was repeated in the other nostril, in a counter-balanced order.

Figure 5:
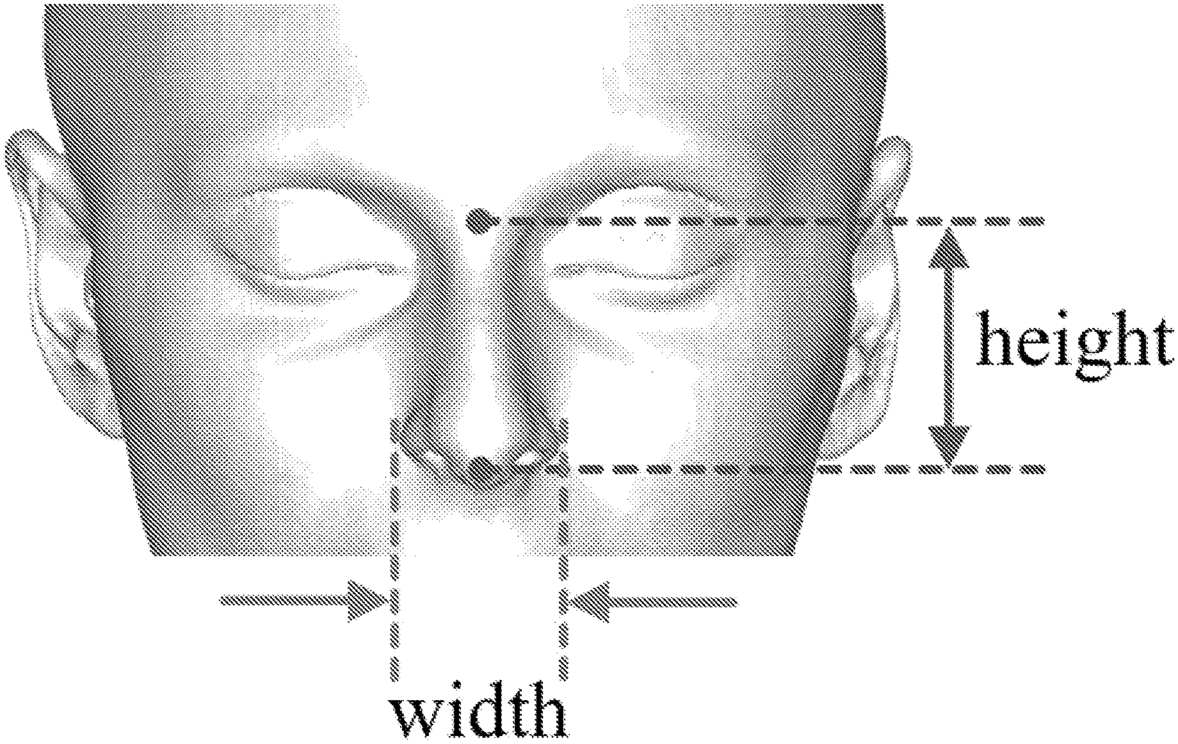
FIG. 5 illustrates the facial reconstruction based on CT scan, and measurement of nasal index as the ratio of external nasal width and height.

Nasal index. The nasal index was determined as the ratio of the external nasal width and height based on CT-reconstructed facial features, as illustrated in FIG. 5.

Rhinometry measurement. The unilaterally minimum (narrowest) cross-sectional area (MCA) in the anterior 5 cm of the nasal airway was determined for each subject using acoustic rhinometry. Nasal resistance during normal breathing was measured unilaterally by anterior rhinomanometry at reference pressure drop of 75 Pa.

CFD modeling. Three-dimensional numerical nasal models that are suitable for numerical simulation of nasal airflow and odorant transport were constructed based on each participant's CT scans, as shown in 6. Briefly, the interface between the nasal mucosa and the air was delineated on the scans (using AMIRA, Visualization Sciences Group). Then, the nasal cavity air space was filled with tetrahedral elements (using ICEM CFD, ANSYS Inc.). A thin (~0.2 mm) region consisting of four layers of compact hybrid tetrahedral/pentahedral elements was created near the mucosal surface to more accurately model the rapidly changing near-wall air velocity and odorant concentration. To achieve grid independent solutions, the computational meshes were refined by gradient adaptation and boundary adaptation protocols. As a result, the final grid consisted of ~1.8-3.5 million elements. Next, inspiratory quasi-steady laminar and turbulent nasal airflow were simulated by applying physiologically realistic pressure drops between the nostrils and the nasal pharynx. A pressure drop of 15 Pa is prescribed for restful breathing and 150 Pa for sniffing. The averaged inspiratory flow rate under 15 Pa among our cohort was 14.5±4.2 L/min, close to the typical range of 15 L/min for restful breathing. The low-Reynolds-number k-ω turbulence model was used to simulate the flow field with a turbulence intensity of 2.5% of the mean velocity imposed at inlet location and compared with the laminar model to investigate possible turbulence effects. The low-Reynolds-number k-o turbulent model has been shown to be valid and reliable in the prediction of laminar, transitional, and turbulent flow behavior. Along the nasal walls, the no-slip boundary condition was applied, and the wall is assumed to be rigid. At the nasopharynx, the "pressure outlet" condition was adopted.

The numerical solutions of the continuity, momentum, and/or turbulence transport equations were determined using the finite-volume method. A second-order upwind scheme was used for spatial discretization. The SIMPLEC algorithm was used to link pressure and velocity. The discretized equations were then solved sequentially using a segregated solver. Convergence was obtained when the scaled residuals of continuity, momentum, and/or turbulence quantities were $<10^{-5}$. Global quantities such as flow rate and pressure on the nasal walls were further monitored to check the convergence.

Data analysis. Prior to data analysis, CFD models of each subject were validated by comparison of cross-sectional cuts with corresponding CT images to ensure the anatomical accuracy of the model. Then, nasal airflow patterns for each subject were simulated and visually inspected. Pearson correlations between each of these independent variables and the dependent variables, odor detection threshold (ODT), were examined. The correlations between the variables were performed unilaterally. All analyses were carried out in IBM SPSS Statistics 22.0 (IBM Corp.).

Results

Figure 7A:
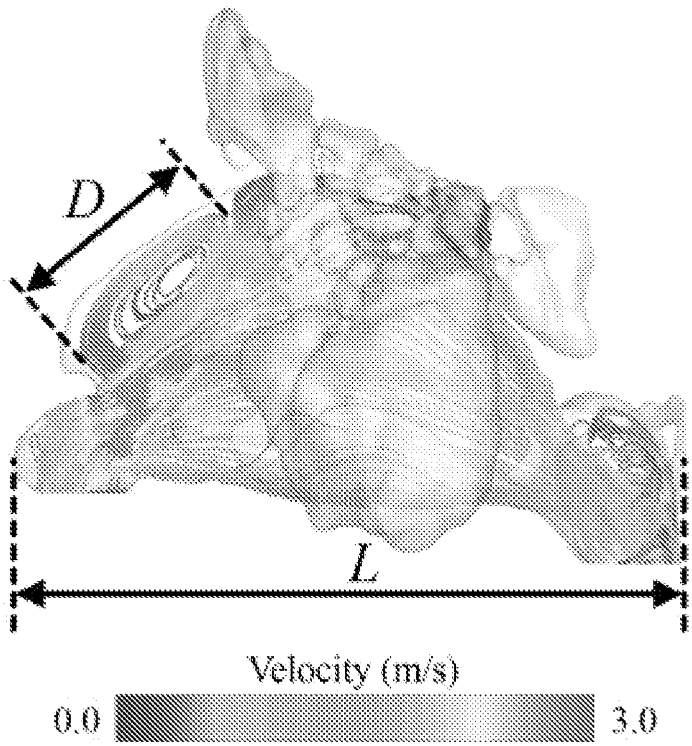
FIGS. 7A-7B show methods used to determine a subject's vortex index (FIG. 7A) and notch index (FIG. 7B). The vortex index is defined as the ratio of vortex length (D) and nasal cavity length (L). The notch index is defined as the ratio of notch depth (h) and nasal cavity length (L).
Figure 9:
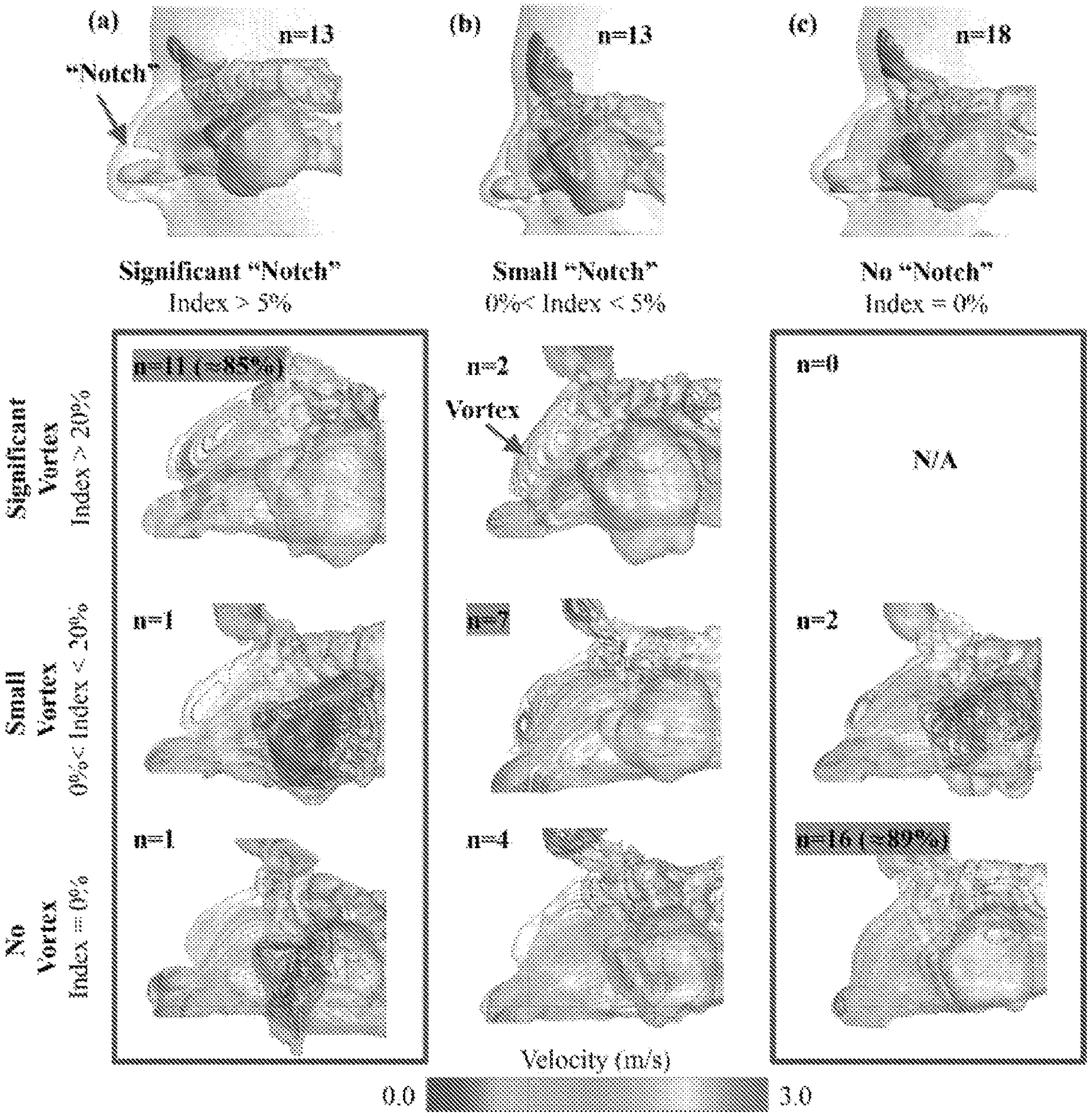
FIG. 9 is a sagittal view showing external nose (gray transparent) and morphology of the nasal vestibule airway (gold solid) for each phenotype. (Panel A) significant notch (notch index>5%). (Panel B) small notch (notch index<5%). (Panel C) no notch (notch index=0%). The "n" values indicate the number of sides that were categorized into each phenotype. Airflow streamline patterns in the nasal cavity were categorized based on the formation of anterior-superior airflow vortex. Depending on its nasal notch index (=0%; <5%; >5%) and vortex index (=0%; <20%; >20%), unilateral nasal cavities were categorized into nine different types. The "n" values indicate the number of sides of all subjects that were categorized into each type.
Figure 10A:
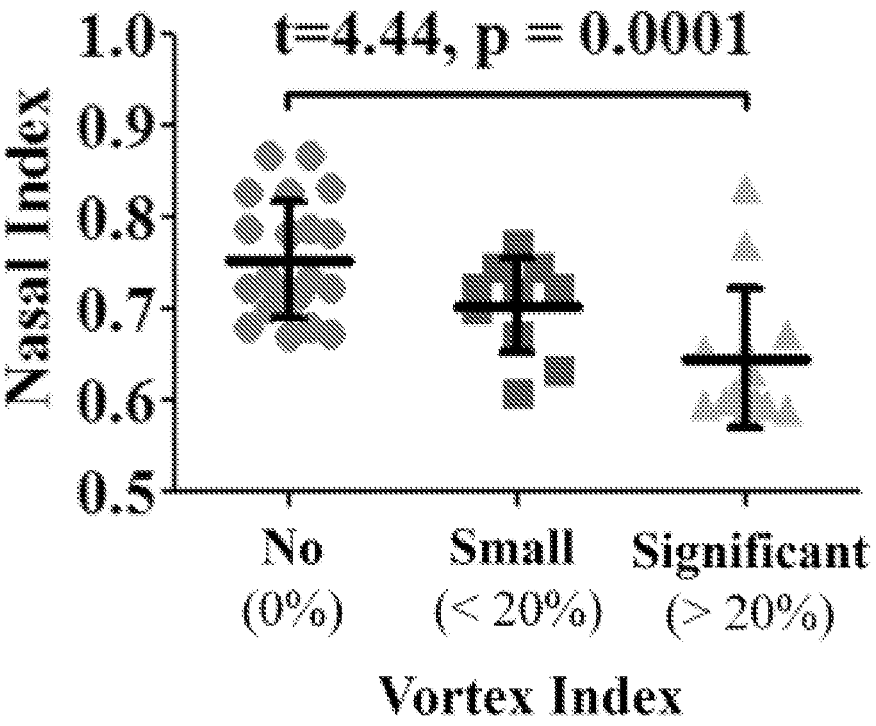
FIGS. 10A-10B are plots showing the nasal index distribution for all subjects with various scores of the vortex index (FIG. 10A) and notch index (FIG. 10B). The nasal index for the subjects with significant vortex (vortex index>20%) was significantly lower than that of the subjects with no vortex (vortex index=0%) in their nasal airflow. Similarly, the nasal index for the subjects with significant notch (notch index>5%) was significantly lower than that of the subjects with no notch (notch index=0%) for their nasal anatomy.
Figure 10B:
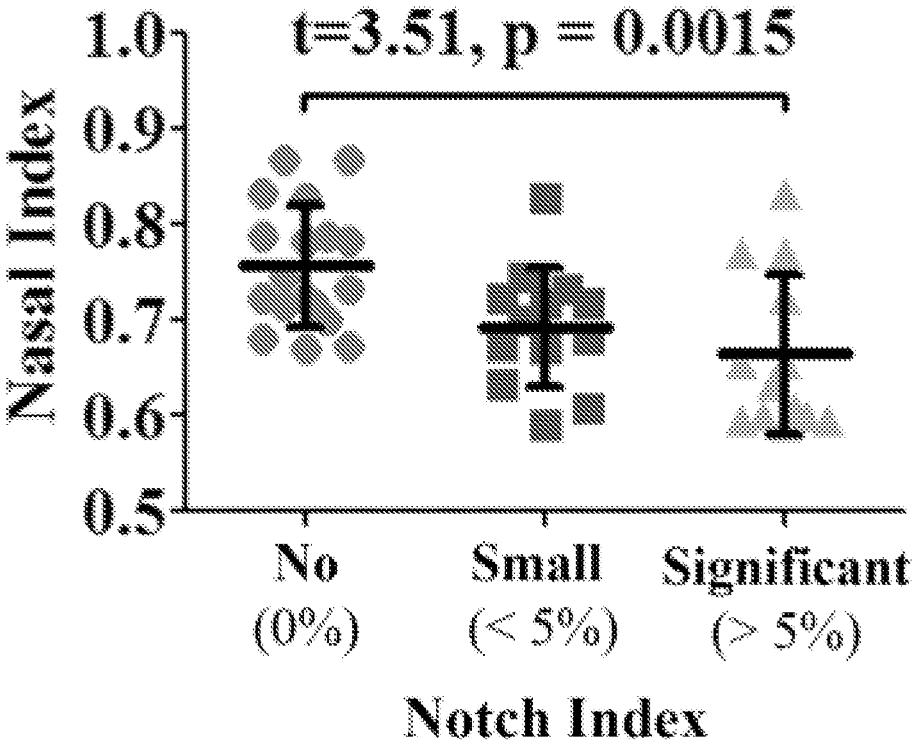

Nasal geometries and airflow patterns. Flow patterns inside the nasal cavity of each subject were characterized and visualized with airflow streamline, generated with neutral-buoyant tracking particles uniformly released on the nostril plane. To visualize airflow streamlines, 300 tracking seeds were uniformly released for each subject and for each side of nostril. While several features of the streamline patterns were found to vary across the subjects, the most prominent variation was the formation of an anterior dorsal vortex, right after the nasal valve, which was found in some subjects but not in others. To quantify the size of the vortex, a vortex index is defined as the maximum vortex length (D) normalized by the nasal cavity length (L) for each subject, as shown in FIG. 7A (Vortex Index=D/L). We further categorized the vortex index as significant vortex (vortex index>20%), small vortex (0%<vortex index<20%), and no vortex (vortex index=0%), as shown in FIG. 9. These categories were used to facilitate better description and sample selection for figure plotting. In the correlation analyses below, it was the continuous vortex index that was used, not the categories. The formation of this anterior dorsal vortex may be due to the narrowing of the nasal valve and abrupt volume increase downstream. The distribution of unilateral vortex indices (significant vortex, n=13; small vortex, n=10; no vortex, n=21) confirmed that this vortex is quite common among healthy cohort. A significant correlation (FIG. 13) was found between the vortex index and nasal index (r=−0.59, P<0.001), indicating that a narrower anterior nasal morphology may result in a more intense airflow vortex.

Figure 7B:
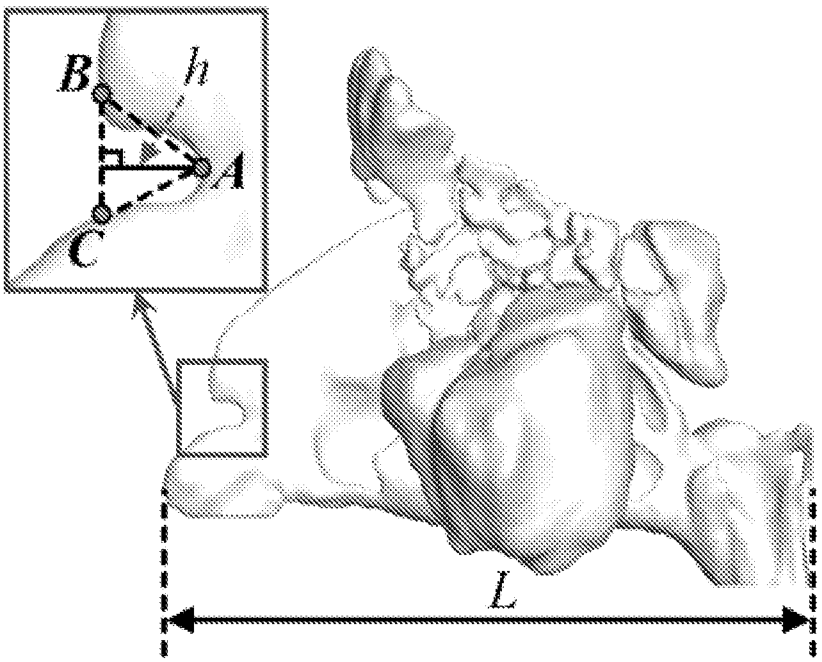
Figure 8:
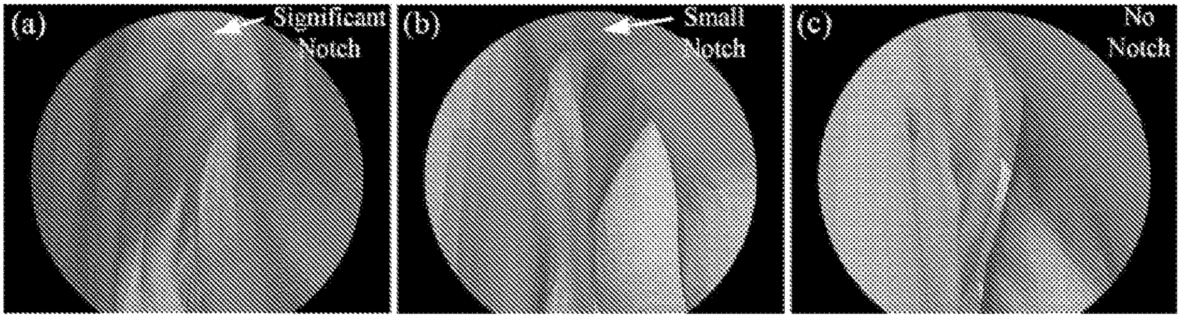
FIG. 8 shows endoscopic views of the nasal valve region of a significant (Panel A), a small (Panel B), and an absence of notch (Panel C). The views are generated by ParaView 5.1.2 (Kitware Inc.) based on CT scan.

We hypothesized that another nasal anatomical feature—partial narrowing of the superior nasal valve, termed a "notch"—may promote vortex formation at the anterior dorsal airspace. To quantify the size of the nasal notch, we first defined the deepest point of the notch (point A in FIG. 7B), then drew the tangential line along the curvature of the anterior dorsal geometry (line BC in FIG. 7B). The notch depth (h) was measured as the perpendicular distance from point A to line BC. A notch index was determined as the ratio of notch depth and nasal cavity length (notch index=h/L). We further categorized the degree of the notch as significant notch (notch index>5%), small notch (0%<notch index<5%), and no notch (notch index=0%). FIG. 8 shows examples of subjects with (Panel A) a significant notch, (Panel B) a small notch, and (Panel C) no notch in endoscopic view simulated by the software ParaView 5.1.2 (Kitware Inc.) based on CT scans. The distribution of unilateral notch indices (significant notch, n=13; small notch, n=13; no notch, n=18) confirmed that a notched nasal phenotype is quite common in this population—59% of subjects have different levels of notch (notch index>0%). Again, these categories were only used to facilitate better description and sample selection for figure plotting. In all the data analyses below, it was the continuous notch index that was used, not the categories. A significant correlation was found between notch and vortex indices (r=0.76, P<0.001), indicating that subjects with pronounced "notches" were more likely to form an airflow vortex. As shown in FIG. 9, 85% of subjects with a significant notch also formed a significant anterior dorsal vortex in the nasal cavity, and 89% of subjects who did not possess a notch did not show any vortex formation.

Figure 6:
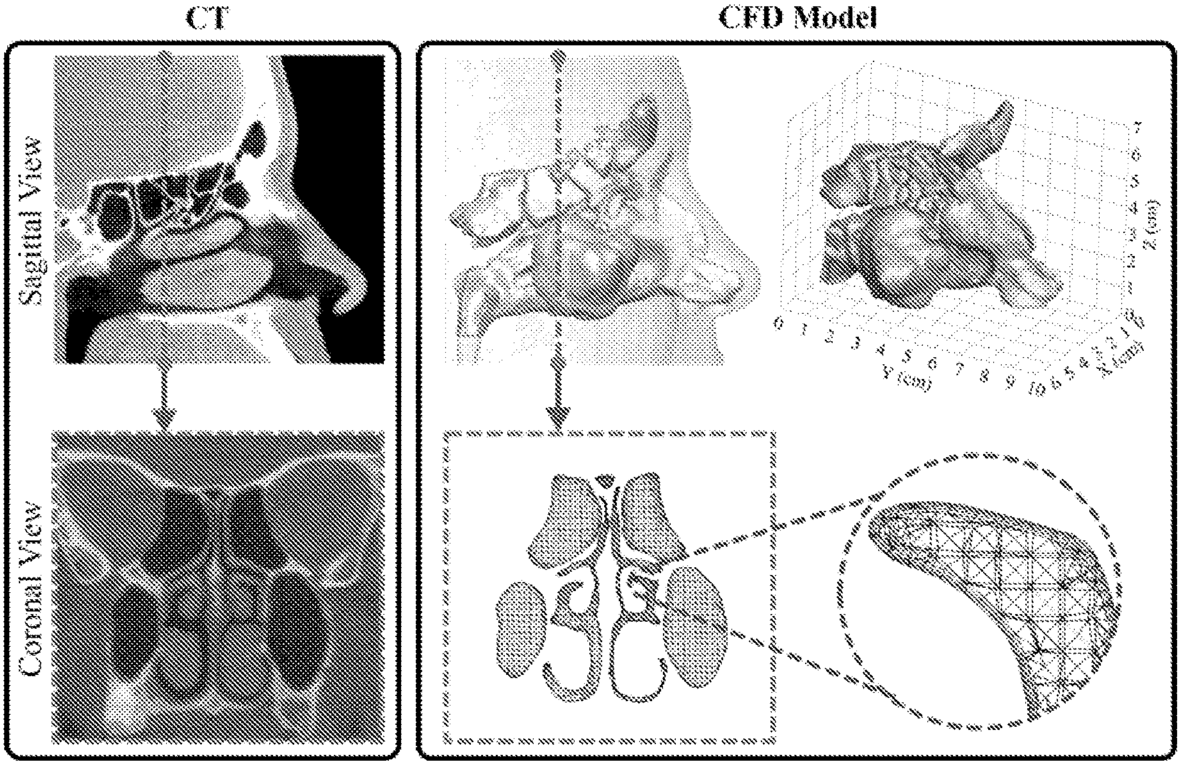
FIG. 6 illustrates a CT-based computational model used to evaluate nasal anatomy. A side-by-side comparison of the CT scan and CFD model from sagittal and coronal views, respectively, are shown. The dashed line indicates the slice cut on the sagittal plane. The perspective view of the 3D model and its dimensions are shown on the right top plot. In a close-up view (right bottom), layers of small and fine elements along the wall can be seen; these capture the rapid near wall changes of air velocity and odorant concentration and are essential for accurate numerical simulations.

The average nasal index in our sample (range from 0.59 to 0.87, with a mean of 0.71, median of 0.72, and SD of 0.08) was indicative of a leptorrhine nose (tall and narrow), which is consistent with the majority Caucasian composition of our subjects. A significant correlation was found between nasal index and notch index (r=−0.56, P<0.001, see FIG. 13). As illustrated in FIGS. 6A-6B, it also appears that a narrower and taller external nose is more likely to have a pronounced notch, which may in turn lead to flow separation and formation of the vortex. Furthermore, the experimentally measured MCA significantly correlated with nasal index (r=0.56, P<0.001), notch index (r=−0.54, P<0.001), and vortex index (r=−0.47, P=0.001). However, nasal resistance showed no significant correlations with any of those measures.

Figure 11A:
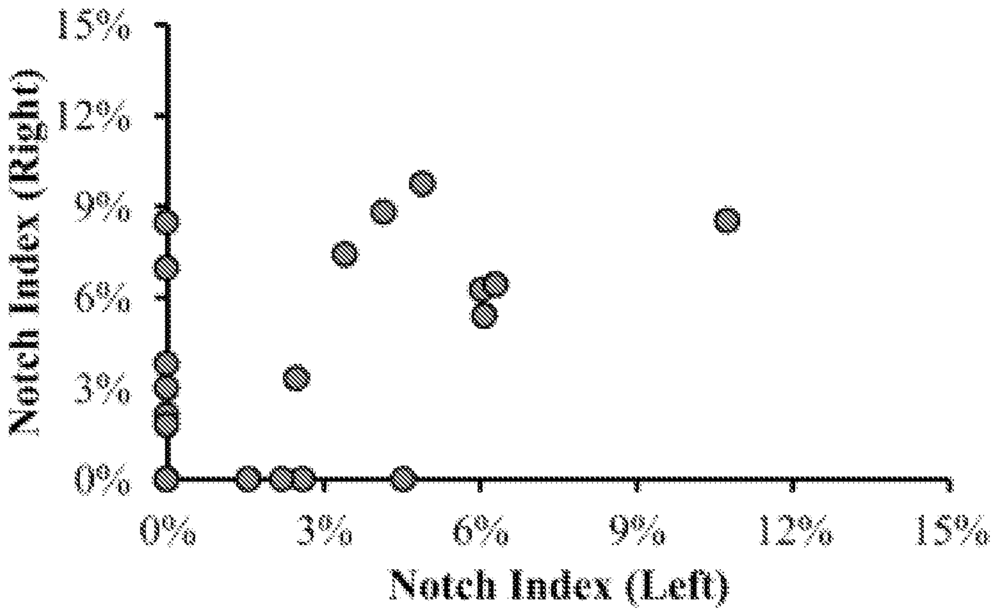
FIGS. 11A-11B show scatter diagrams of the notch index (FIG. 11A) and vortex index (FIG. 11B) between left and right side of the same subjects. Among 22 tested healthy controls, there was no significant correlation between left and right side of the nose for either the notch index or the vortex index.
Figure 11B:
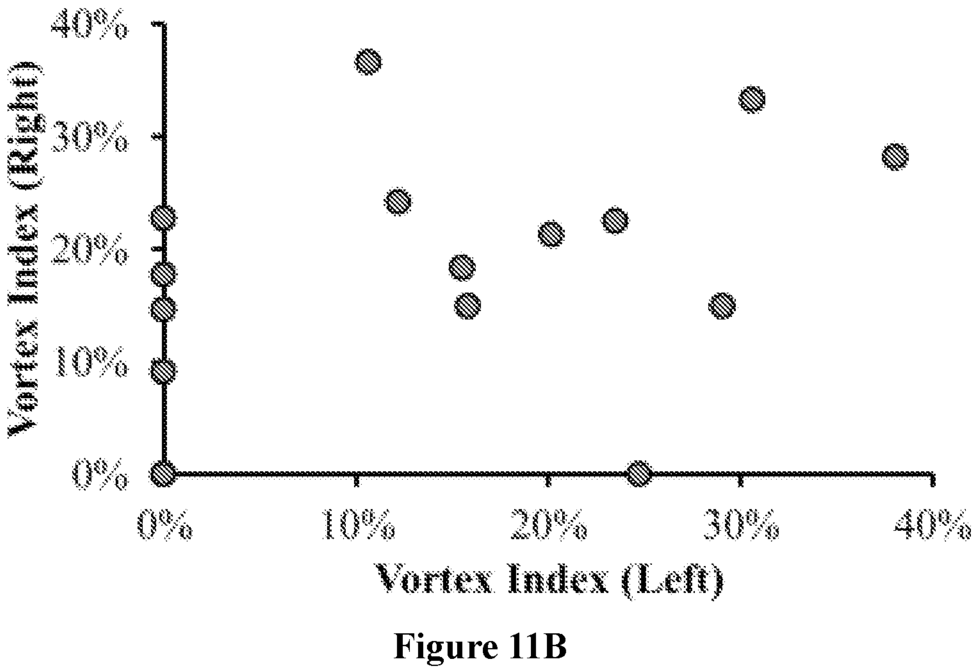

To address the concern of treating the notch and vortex indices from each side of the nose as independent variables, we examined the correlations between the left and right sides of the same patients and found no significant correlation, as shown in FIGS. 11A-11B, reflecting significant unilateral differences. Among the 22 healthy subjects tested, 59.1% of total subjects had different notch categories between the two sides, and 31.8% had different vortex categories. With the exception of the nasal index, all variables collected in the study were unilateral. Thus, to potentially capture any unilateral differences as well as in consideration of the fact that two sides of the nose are parallel passages—that aerodynamics features on one side should not substantially affect the other—all data analyses were carried out unilaterally, with the same nasal index value assigned to both sides.

Impacts on olfactory function. We further examined the relationship between each of these anatomical and aerodynamic variables and the dependent variables of measured ODT among the subjects. Significant correlations were found between ODT of L-Carvone and both vortex index ($r=0.31$, $P=0.0498$) and notch index ($r=0.33$, $P=0.032$). A significant correlation was also found between ODT of PEA and the notch index ($r=0.32$, $P=0.034$). However, ODT of D-Limonene, a lower mucosal soluble odor, did not correlate with either notch index or vertex index.

As shown in FIG. 12, subjects with a significant notch (notch index>5%) had significantly better olfactory detection thresholds for L-Carvone ($P=0.021$) and for PEA ($P=0.04$) than did those with no notch, but not for D-Limonene (see Panels A-C). Similarly, if we group the subjects according to the vortex index, Panels D-F illustrate that subjects with a significant vortex (vortex index>20%) have better olfactory detection thresholds for L-Carvone ($P=0.023$) and PEA ($P=0.054$, strong tendency), but not for that of D-Limonene than do subjects with no vortex. These findings indicate that a higher notch index (greater narrowing in the nasal vestibule regions) and higher vortex index (more intense superior airflow vortex) may result in better olfactory sensitivity. ODT of D-Limonene, a low mucosal soluble odor, does not correlate with any of the anatomical or aerodynamic variables, even though ODTs of PEA, L-Carvone, and D-Limonene correlated significantly with each other, as expected. No significant correlation was found between nasal resistance, nasal index, or MCA and any of the olfactory thresholds.

The above analyses were repeated for higher inspiratory flow rate at 150 Pa by applying the low-Reynolds-number k-o turbulence model, and the results were consistent with those found with restful breathing flow rates. Analyses were also repeated excluding the two non-Caucasian subjects, and no substantial changes in findings were observed.

Discussion

Normative variations in anatomical features of the nasal airway have been widely reported in the past. The nasal index (width/height) is known to show significant racial variation. A typical Caucasian nose has a nasal index less than 0.70 (also described as leptorrhine). A nasal index between 0.70 and 0.85 is described as messorhine. A platyrrhine nose has a nasal index greater than 0.85. The difference in nasal index among populations may be the result of adaptations to climate, evolutionary factors, or simply genetic drift. In addition, distinct internal nasal vestibule structures ("notch") were also found within a small sample of human noses. In this Example, we further quantified the degree of the nasal notch and found it significantly correlated with the nasal index ($r=-0.56$, $P<0.001$). This negative correlation indicates that a narrow nose is more likely to present with a notch in the nasal valve region than is a broad nose. In addition, both the nasal index and notch index were found to correlate significantly with nasal MCA ($r=0.56$, $P<0.001$; $r=-0.54$, $P<0.001$). However, neither the nasal index nor the notch index correlated significantly with nasal resistance.

Normative variations in the aerodynamic features of the nasal airway have also been implicated in the past. The formation of an anterior-superior airflow vortex was first reported in 1977 in a case report of one healthy subject. On the basis of simulation in one subject, it was speculated that the formation of such an airflow vortex may be due to narrowing of the nasal valve and an abrupt volume increase after the nasal valve. It was later confirmed that such airflow variations are widely present in healthy subjects. The current study provides the first connection between these aerodynamic and anatomical features: a strong correlation between lower nasal index, lower MCA, higher "notch," and the more likely formation of the anterior-superior airflow vortex. The abrupt volume changes before and after the "notch" could induce airflow recirculation—hence the vortex. Consequently, the majority (85%) of nasal airways with a significant nasal "notch" appear to have an airflow vortex ipsilaterally (FIG. 9).

However, there is a continuing debate on the functional relevance of these internal nasal anatomy variations and their associated airflow patterns within a healthy population. Some have suggested these are simply the result of genetic drift. It is well recognized that human olfactory acuity has significant variability within a normal population, with much research focused on receptor genetics and postreceptor neural variations. It has also been hypothesized that nasal anatomical and aerodynamic variations may potentially benefit olfactory sensitivity. This study provides the first direct evidence of the potential impact of normal variation in nasal structure and aerodynamics on normative variations in olfactory sensitivity. It suggests that a "notch" in the nasal vestibule region may improve olfactory sensitivity to some odorants, potentially due to the formation of an airflow vortex in the nasal valve region. The airflow vortex may promote odor plume mixing, increase its resident time within the olfactory region, and benefit odorants with high mucosal solubility. In contrast, sorption of less soluble odorants seems to be only limited physically by their low solubility and not affected by increased flow rate or resident time. This finding may have broad implications. Variations contributed by differences in internal nasal anatomy and aerodynamics may need to be accounted for, for example, in screening for subjects when investigating olfactory function, or screening for sensory panels in flavor and fragrance research depending on the solubility profiles of the flavors and fragrances. It also remains to be investigated whether the anatomical and aerodynamic variations would make a subset of the population more susceptible to obstruction-related olfactory losses or damage from inhaled toxins.

The lessons learned here may also be applicable to bio-inspired artificial noses. Aerodynamics is central to olfaction because it plays a vital role in odor sampling. To provide the best opportunity for odorant molecules to contact the sensory epithelium, an artificial olfaction device could either increase sensor surface area or increase the odorant resident time within a limited nasal volume. Creating an airflow recirculation may benefit detection by increasing odorant resident time, especially for odorants with high solubility.

Example 2: Devices and Methods for Improving Olfaction

Olfaction starts with the transport of volatile chemical molecules by air flow to the olfactory epithelium, which is confined to a remote and small region of the human nasal cavity. Maintaining sufficient amounts of odorant transport from the ambient environment to the olfactory epithelium is a critical prerequisite for olfactory function. Yet, during a normal breath, less than 15% of the air inhaled through the nose reaches the olfactory epithelium.

In this Example, we design and evaluate devices that improve olfaction by modulating nasal airflow and enhancing odor delivery to the olfactory region. Specifically, we evaluate two devices: (1) a nasal foam plug with a diagonal channel embedded, which when inserted into the nares of a subject and directed upwards, can enhance air/odor flow superiorly to the olfactory region, which we further confirmed using computational modeling; and (2) a nasal clip that constricts a subject's upper nasal vestibule cartilage region to create a "notch" in the upper nasal valve region without completely blocking the nose, a key region identified in Example 1, which can intensify the nasal airflow vortex and improve olfactory sensitivity.

We tested these two manipulations on 61 healthy controls and measured odor detection threshold for phenylethyl alcohol (PEA), without interventions, with a "pinch" conferred by a nasal clip to create or enhance a "notch", and with a nasal plug inserted up and down, in counterbalanced order. A significant correlation was found between degree of olfactory improvement and baseline olfactory sensitivity ($r=-0.45$, $p<0.005$), with the most improvement in subjects with less sensitive smell function to begin with. This makes sense—as an analogy, corrective lenses may have limited effect on a perfect 20/20 vision but can significantly improve suboptimal vision. To confirm this observation, we divided our sample based on baseline PEA thresholds (normative cutoff>=8), into "average" (PEA 8-16.5, n=30) and "highly sensitive" (PEA>16.5, n=28); the improvement in PEA thresholds was significant only in the average group (baseline 12.5±2.8, pinch 14.6±5.4, plug 14.4±4.9, $p<0.05$), not among the "highly sensitive" group. Both the "nasal plug" and "pinch"/nasal clip ideas are counterintuitive, as they actually limit total nasal airflow during breathing or sniffing, and thus the enhancement is likely due to more effective redirected or intensified airflow vortex toward the olfactory region.

These results demonstrate a strategy for improving olfactory function by peripheral modulation of nasal/odor airflow, which may inspire future integrative biological and neuroethology investigations. By understanding the impact of nasal anatomy and its modulation on transport odorant with varying physiochemical property we can better improve olfactory function through peripheral mechanisms. Devices to enhance nasal airflow and olfactory odor delivery may have broad applications to professionals who rely on olfaction for their job functions (chefs, perfumers, food/wine critics, fragrant designers, sensory testing experts, etc.), as well as to general public who want to better enjoy olfactory experiences (food, fragrance, etc.), and to patients with conductive smell loss.

Details

Human olfactory acuity has significant normative variability. We therefore asked whether any portion of the variation could be accounted for by the normative variation in internal nasal anatomy and aerodynamics. Healthy volunteers (n=22) underwent CT scans for CFD modeling of nasal airflow patterns. Unilateral ODTs for phenylethyl alcohol (PEA), l-carvone, and d-limonene (from high to low mucosal solubility) were obtained. We hypothesized that the sorptive properties would make them more or less susceptible to airflow changes. We observed significant normative variations in both nasal anatomy and aerodynamics.

The most prominent was the formation of an anterior-dorsal airflow vortex in some but not all subjects (FIG. 16, Panel A), with the vortex size (D normalized by the nasal cavity length (L)) significantly correlated with the ODT of l-carvone ($r=0.31$, $p<0.05$). The formation of the vortex is likely the result of anterior nasal morphology, with vortex size correlated significantly with a nasal vestibule "notch" index ($r=0.76$, $p<0.001$). The notch is a narrowing of the upper nasal vestibule cartilage region (FIG. 16, Panel B). The degree of the notch, indexed as the ratio of notch depth and nasal cavity length (Notch Index=h/L), also significantly correlates with the ODT for PEA ($r=0.32$, $p<0.05$) and l-carvone ($r=0.33$, $p<0.05$). The ODT of d-limonene, a low-mucosal-soluble odor, did not correlate with any of the anatomical or aerodynamic variables. Nasal resistance also did not correlate to any ODTs.

These results suggested that a narrower vestibule region (notch) may intensify the airflow vortex toward the olfactory region and significantly affect olfactory sensitivity to high-mucosal-soluble odors independent of global nasal airflow rate or resistance (FIG. 16, Panel C and Panel D).

We then investigated whether a nasal clip (similar to what synchronized swimmers use) could be applied to a subject's nose to create/pinch an artificial notch, without completely blocking the nose, to improve olfaction (FIG. 16, Panel E). As shown in FIG. 16, Panel F, the nasal clip significantly improved olfactory sensitivity for subjects with moderate baseline PEA thresholds (8-16.5) but not for those highly sensitive (>16.5).

Figure 15A:
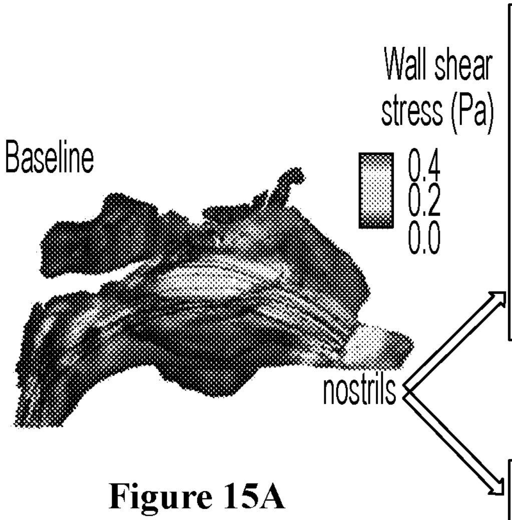
FIG. 15 illustrates how the nasal plug directs airflow when present in the nares of a subject. As shown in Panel (C), when the nasal plug is inserted pointing "up," it directs airflow up toward the olfactory region.
Figure 15B:
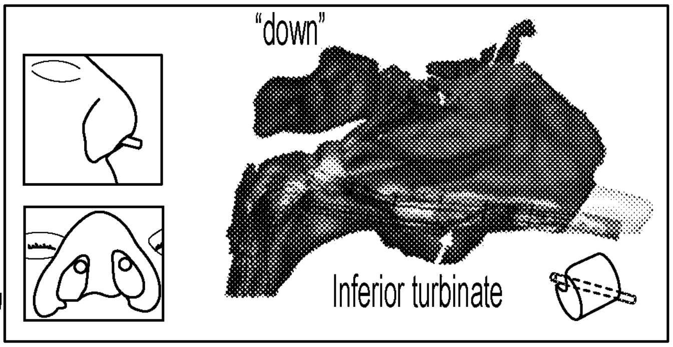
Figure 15C:
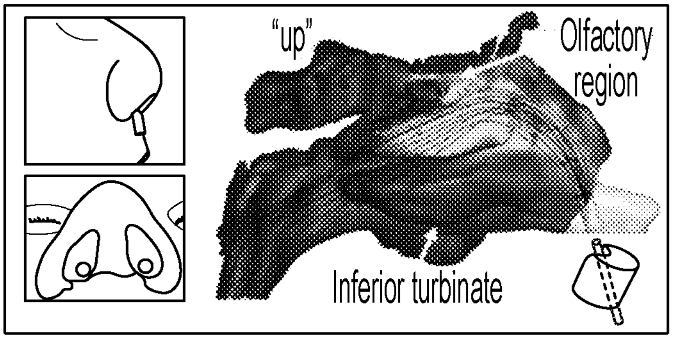
Figure 16A:
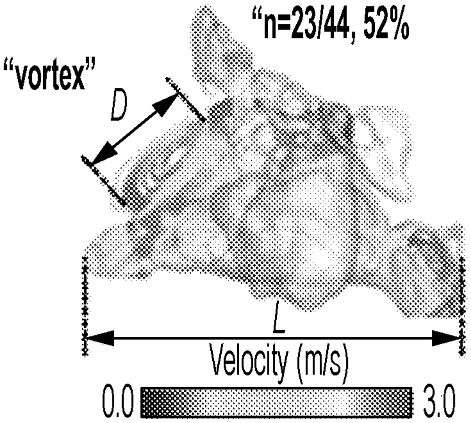
FIG. 16 shows the variation of anterior nasal airflow vortex in some but not all healthy controls (Panel A), which is linked to a nasal vestibule "notch" (Panel B). As shown in Panel C and Panel D, a narrower vestibule region (high "notch") likely intensifies the airflow vortex toward the olfactory region, leading to better olfactory sensitivity to l-carvone. A nasal clip pinches the nose to create an artificial notch (Panel E) that improve olfactory sensitivity (Panel F) for subjects with moderate baseline PEA thresholds (8-16.5) but not for those highly sensitive (>16.5).
Figure 16B:
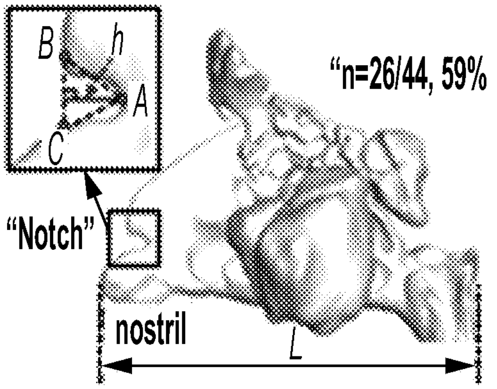
Figure 16C:
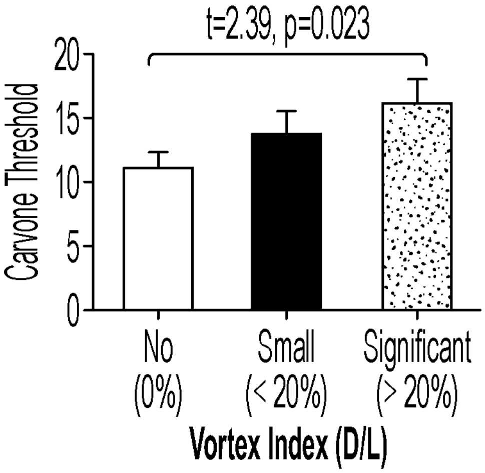
Figure 16D:
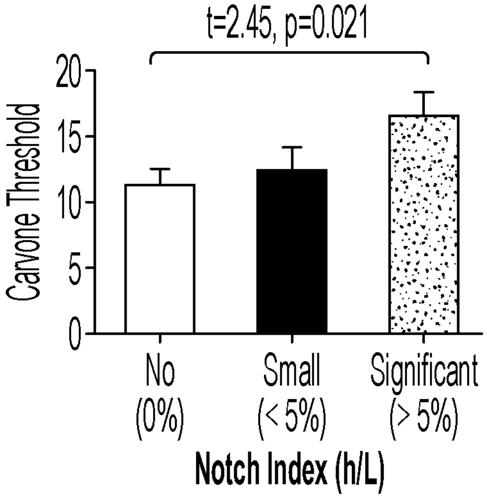
Figure 16E:
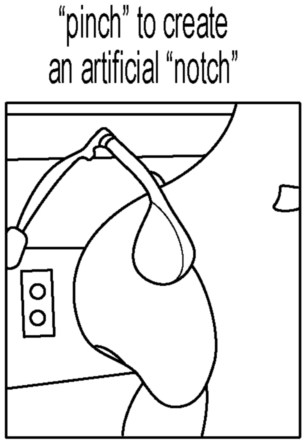
Figure 16F:
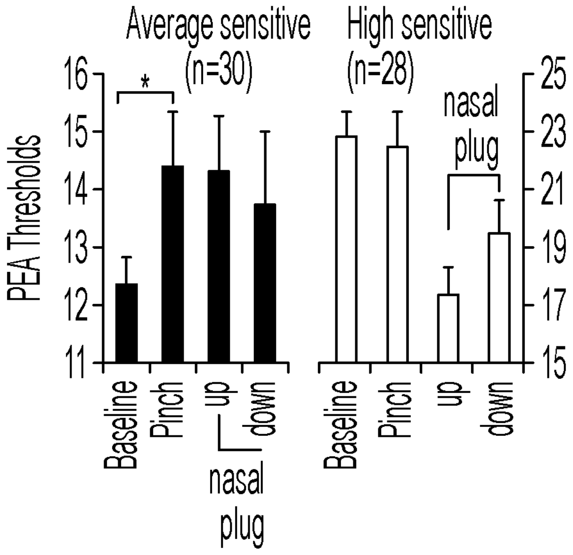

We also considered whether a nasal plug (see FIGS. 14A-14D) could be used to enhance olfaction by enhancing olfactory airflow. As shown in FIG. 15, when the nasal plug is inserted in the nares pointing "up" (Panel C), it essentially directs airflow up toward the olfactory region. As shown in FIG. 16, Panel F, this can improve olfactory sensitivity. Conversely, when the nasal plug is inserted in the nares pointing "down" (Panel B), the plug directs airflow away from the olfactory region. This can decrease olfactory sensitivity.

We will further investigate the potential of improving olfactory function by peripheral modulation of nasal/odor airflow. Both the "nasal aid" and "pinch" ideas are counterintuitive, as they actually limit total nasal airflow during breathing or sniffing, and thus the enhancement is likely due to more effective redirected or intensified airflow vortex toward the olfactory region. We will examine if a particular baseline nasal anatomy might be required for greater effect, for example, whether someone with a preexisting nasal notch benefits less from the artificial notch than someone without a preexisting nasal notch.

Extending the analogy that corrective lenses are more effective to improve suboptimal vision, we further hypothesize that modulating nasal/odor airflow may effectively improve airflow to the olfactory region in patients with conductive olfactory loss or with some underlying airway constriction. We will use CFD modeling to determine which of these manipulations better enhance airflow to the olfactory region based on individual anatomy. We will examine the range of the effectiveness of manipulation based on the odorants' physical properties. By better understanding the impact of nasal anatomy and its modulation on transport odorant with varying physiochemical properties, we can better improve olfactory function through peripheral mechanisms.

Figure 17:
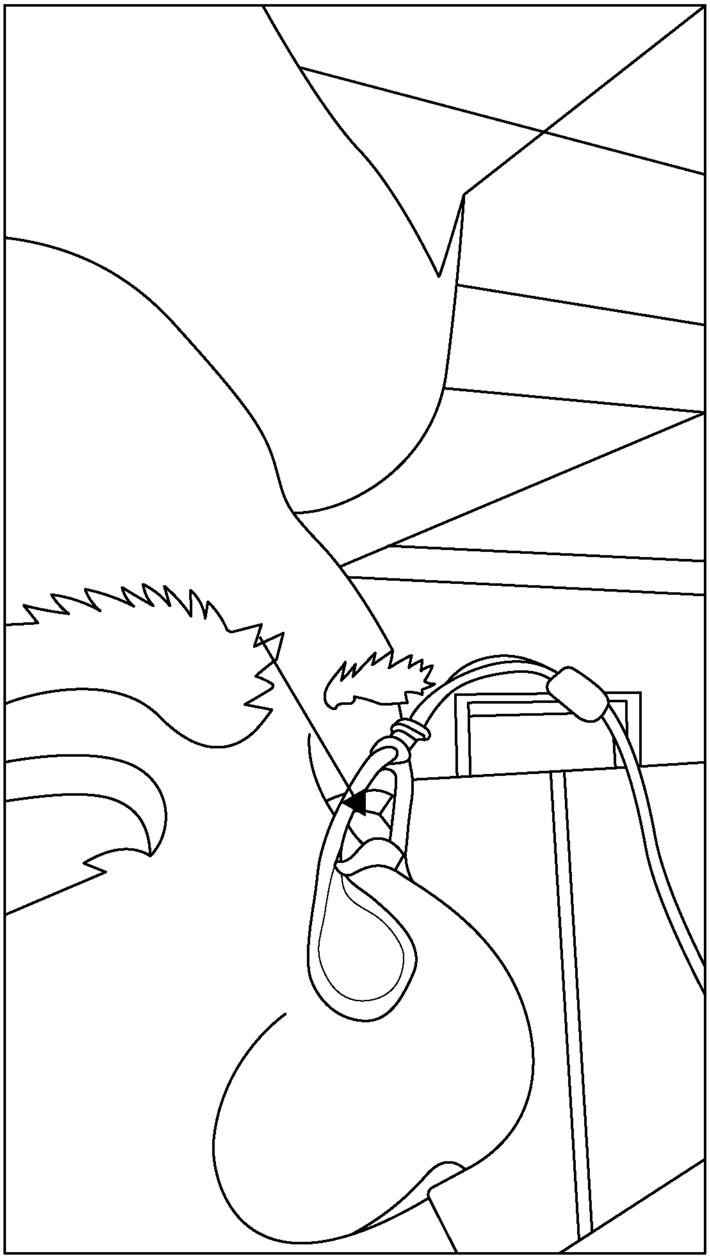
FIG. 17 shows an example nasal clip including an adjustable retention band (indicated by the arrow) that guides seating and positioning of the nasal clip on the nose of a subject.

Various nasal clip designs are suitable for use in modifying olfaction, provided that the clip is dimensioned to create a pinch in the upper nasal vestibule region without completely blocking nasal airflow. In some designs, the mechanical force that serves to pinch the nose can be provided, solely or primarily, by an outer nasal clip frame. In some designs, the outer nasal clip frame can be formed (wholly or in part) from a metal (e.g., aluminum, stainless steel, titanium, or an alloy thereof) or a polymer (e.g., a rigid thermoplastic). In some designs, the outer nasal clip frame can be generally u-shaped. In some designs, the nasal clip can further comprise an adjustable retention band that guides seating and positioning of the nasal clip on the nose of a subject as shown in FIG. 17. The retention band can be adjusted to control the amount of pressure that the nasal clip applies to the subject's upper nasal vestibule cartilage (and by extension the how much the subject's upper nasal vestibule is constricted). Likewise, the outer nasal clip frame can be deformable, elastic, or springable, if desired, with varying designs providing for amounts of pressure to be applied the subject's upper nasal vestibule cartilage when the nasal clip is in use (and by extension provide varying degrees of constriction to the subject's upper nasal vestibule).

As for the degree of pinch necessary for a good effect with respect to enhancing smell function, in some examples a pinch of at least 15% up to 60% of the height of external nose provides for effective enhancement of olfaction. For example, if the subject's external nose is 2 cm tall, then a pinch of from about 0.3 cm up to about 1.2 cm can be suitable. If the subject's external nose is 4 cm tall, then a pinch of from about 0.6 cm up to about 2.4 cm can be suitable. In general, a taller external nose calls for a larger pinch (in absolute dimension).

The nasal plugs described herein can also be used in the down direction to alleviate symptoms of parosmia and/or phantosmia.

Since its outbreak in China in December 2019, the global impact of SARS-CoV-2 infection has been extraordinary, with over 350 million cases and more than 5.5 million lives lost (WHO Coronavirus Dashboard, January 2022). Alteration of olfactory function (smell) emerged as a hallmark symptom of COVID-19 that over 50% of COVID-19 patients self-reported smell loss; this increases to 86% in studies using validated psychophysical measurements. In approximately 15% of COVID-19 patients, persistent smell loss lasting >90 days has been noted. COVID-19 patients also self-report much higher incidence (7-11%) of parosmia (distorted odor perception) and phantosmia (odor perception, usually foul, in the absence of odorant) than do typical viral infection patients. And more than 50% of the parosmia and phantosmia cases persisted over 90 days.

The nasal clips and nasal plugs inserted in the nares pointing "up" can serve to enhance olfactory function among those COVID-19 patients with olfactory losses.

Further, nasal plugs inserted in the nares pointing "down" can alleviate parosmia and phantosmia symptoms. For these patients, the olfactory perception has been distorted and become unpleasant. The nasal plug can be used to divert nasal airflow from the olfactory region, thereby reduces unpleasant olfactory perception.

We have tested this concept on one subject with long COVID-19 related phantosmia. Prior to insertion of the nasal plug, this subject consistently reported smelling a foul odor, even when breathing in clean room air (she rated this odor as a 7 (0-10) in discomfort). Upon insertion of the nasal plug in the down position, she reported a 2 in discomfort, a significant improvement.

The nasal plug can thus serve multiple functions: directed upwards, it enhances airflow to the olfactory region and enhances olfactory perception; directed downwards, it reduces airflow to the olfactory region and reduces olfactory perception, potentially bad odor perception. Thus, it can be applied beyond parosmia and phantosmia patients to anyone who wants to get rid of bad odor perception, for example: an unavoidable environmental odor (close to sewer, close to farm/factory). It allows you to breathe air naturally through your nose, while reducing unpleasant odor perception.

The devices and methods of the appended claims are not limited in scope by the specific devices and methods described herein, which are intended as illustrations of a few aspects of the claims. Any devices and methods that are functionally equivalent are intended to fall within the scope of the claims. Various modifications of the devices and methods in addition to those shown and described herein are intended to fall within the scope of the appended claims. Further, while only certain representative components, features, and method steps disclosed herein are specifically described, other combinations of the components, features, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A nasal clip for enhancing intranasal air and odorant delivery patterns, the nasal clip comprising: an outer clip frame comprising a first arm terminating in a first nose pad and a second arm terminating in a second nose pad, wherein the outer clip frame approximates a U-shape; wherein the first nose pad and the second nose pad are spaced apart by a first distance that is configured to allow arrangement of the nasal clip on a nose of a subject in a manner as to pinch an upper nasal vestibule cartilage of the subject at least 15% up to 60% of a height of the nose of the subject, constricting the upper nasal vestibule of the subject to form an artificial notch therewithin in a manner as to increase a notch index of the subject's vestibule airway by at least 20% without completely blocking nasal airflow; and an adjustable retention band comprising a compliant material, wherein the retention band is coupled to the first arm and the second arm in a manner that the retention band spans between the first and second arms at an inward position relative to the outer clip frame, wherein the adjustable retention band is coupled to the outer clip frame at a second distance measured along the first or second arm, respectively, from the first nose pad and the second nose pad, wherein the second distance is configured to allow seating and positioning of the nasal clip on the nose of the subject.

2. The nasal clip of claim 1 wherein the second distance of the retention band is adjustable along the respective first and second arms of the outer clip frame.

3. The nasal clip of claim 2, wherein the first arm and the second arm of the outer clip frame each define a track, wherein a first end and a second end of the retention band are each coupled to and moveable along the corresponding track of the first and second arms.

4. The nasal clip of claim 1, wherein the first nose pad and the second nose pad are sized and spaced apart by the first distance that is configured to allow arrangement of the nasal clip on the subject's nose in a manner as to increase a vortex index of the subject's nasal vestibule airway by at least 20%; reduces the subject's nasal airflow by 15% to 80%; or any combination thereof.

5. The nasal clip of claim 1, wherein each of the first arm and the second arm of the outer clip frame define an opening through which an end of the retention band extends.

6. The nasal clip of claim 5, wherein a portion of the retention band positioned inward relative to the outer clip frame is adjustable via movement of the ends of the retention band through the openings in the first and second arms.

* * * * *